US006414153B1

(12) United States Patent
Kelly et al.

(10) Patent No.: US 6,414,153 B1
(45) Date of Patent: Jul. 2, 2002

(54) 1-PHENYLPYDRROLIDIN-2-ONES AND -THIONES AND 1-(4-PYRIDYL) PYDRROLIDIN-2-ONES AND -THIONES WHICH ARE USEFUL IN THE TREATMENT OF INFLAMMATORY DISEASE

(75) Inventors: Terence Alfred Kelly, Ridgefield; Jiang-Ping Wu; Daniel Kuzmich, both of Danbury; Yancey David Ward, Sandy Hook, all of CT (US); Leah Lynn Frye, Patterson, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/605,584

(22) Filed: Jun. 28, 2000

Related U.S. Application Data

(60) Provisional application No. 60/144,895, filed on Jul. 21, 1999.

(51) Int. Cl.[7] ...................... C07D 471/02; A61F 31/437
(52) U.S. Cl. ...................... 546/113; 548/486; 514/418; 514/300
(58) Field of Search ............. 548/486; 514/418, 514/300; 546/113

(56) References Cited

U.S. PATENT DOCUMENTS

| 3,668,217 A | 6/1972 | Fujinami et al. |
| 3,741,981 A | 6/1973 | Fujinami et al. |
| 3,846,441 A | 11/1974 | Mine et al. |
| 4,911,748 A | 3/1990 | Prisbylla |
| 4,944,791 A | 7/1990 | Schroeder et al. |
| 4,977,270 A | 12/1990 | Wee |
| 5,208,250 A | 5/1993 | Cetenko et al. |
| 5,306,822 A | 4/1994 | Cetenko et al. |
| 5,334,606 A | 8/1994 | MacLeod |
| 5,464,856 A | 11/1995 | Cetenko et al. |
| 5,750,553 A | 5/1998 | Claussner et al. |
| 5,854,232 A | * 12/1998 | Volkmann et al. ........... 514/210 |

FOREIGN PATENT DOCUMENTS

| DE | 19 40 032 A1 | 3/1970 |
| DE | 19 58 183 A1 | 6/1970 |
| DE | 21 00 800 A1 | 7/1971 |
| EP | 0 091 596 A1 | 10/1983 |
| EP | 0 343 643 A1 | 11/1989 |
| EP | 0 545 478 A1 | 6/1993 |
| GB | 1154976 | * 6/1969 |
| JP | 51-88631 | 8/1976 |
| WO | WO95 18794 A1 | 7/1995 |
| WO | WO98 39303 A1 | 9/1998 |
| WO | WO99 11258 A1 | 3/1999 |
| WO | WO99 49856 A2 | 10/1999 |

OTHER PUBLICATIONS

Takayama, et al; "Quantitative Structure–activity Relationships of Antifungal 1–(3,5–Dichlorophenyl)–2,5–pyrrolidinediones and 3–(3,5–Dichlorophenyl)–2,4–oxazolidinediones", Agric. Biol. Chem. 1982, 46, 2755–8.

Ll, et al; "Examination of the Interrelationship Between Aliphatic Group Dipole moment and Polar Substituent Constants" J. Pharm. Sci. 1984; 73, 553–8.

Halim, et al; "3–[2–(3,5–Dimethylpyrazolyl)} Succinic Anhydride: Synthone for the Synthesis of Some Heterocycles with Potential Pharmaceutical Activity"; Monatshefte fuer Chemie, 1994, 125 1437–1442.

Database CA on STN, Chemical Abstracts, (Columbus, OH, USA) No. 128:204801, Hollinshead,S. et al, "Combinatorial process for preparing substituted pyrrolidine libraries", Abstract WO 98 08813, Mar. 1998.

Database CA on STN, Chemical Abstracts, (Columbus, OH, USA) No. 124:145896, Drewes, M. et al, "Preparation of 4–(heterocyclo)–2–(sulfonamido) benzonitrile selective herbicides", abstract DE4414568, Nov. 1995.

Musza, L. L., et al, "Potent New Cell Adhesion Inhibitory Compounds from the Root of Trichilia rubra"; Tetrahedron, 1994, 50, 11369–11378.

(List continued on next page.)

Primary Examiner—Floyd D. Higel
Assistant Examiner—Kamal Saeed
(74) Attorney, Agent, or Firm—Robert P. Raymond; Alan R. Stempel; Mary-Ellen M. Devlin

(57) ABSTRACT

Novel compounds of the formula I:

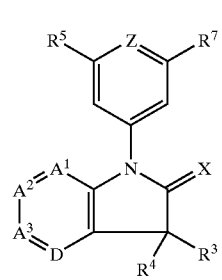

which are useful for treating or preventing inflammatory and immune cell-mediated diseases. Exemplary compounds are:

3-(4-bromobenzyl)-1-(3,5-dichlorophenyl)-1,3-dihydroindol-2-one;

3-(4-bromobenzyl)-1-(3,5-dichlorophenyl)-3-methyl-1,3-dihydro-indol-2-one;

3-benzyl-1-(3,5-dichlorophenyl)-3-methyl-1,3-dihydroindol-2-one;

3-(4-bromobenzyl)-1-(3,5-dichlorophenyl)-4-hydroxy-3-methyl-1,3-dihydroindol-2-one; and, 3-(4-bromobenzyl)-1-(3,5-dichlorophenyl)-5-fluoro-1,3-dihydroindol-2-one.

14 Claims, No Drawings

OTHER PUBLICATIONS

Boschelli, D. H., et al; "3–Alkoxybenzo[b]thiophene–2–carboxamides as Inhibitors of Neutrophil–Endothelial Cell Adhesion"; J. Med. Chem, 1994., 37, 717.

Boschelli, D. H., et al; "Inhibition of E–Selectin–, ICAM–1–, and VCAM–1–Mediated Cell Adhesion by Benzo[b]thiophene–, Benzofuran–, Indole–, and Naphthalene–2–carboxamides: Indentification of PD 144795 as an Antiinflammatory Agent"; J. Med. Chem., 1995, 38, 4597–4614.

Sanfilippo, P. J., et al; "Novel Thiazole Based Heterocycles as Inhibitors of LFA–1/ICAM–1 Mediated Cell Adhesion"; J. Med. Chem. 1995, 38, 1057–1059.

* cited by examiner

# 1-PHENYLPYDRROLIDIN-2-ONES AND -THIONES AND 1-(4-PYRIDYL) PYDRROLIDIN-2-ONES AND -THIONES WHICH ARE USEFUL IN THE TREATMENT OF INFLAMMATORY DISEASE

RELATED APPLICATIONS

The benefit of prior provisional application Ser. No. 60/144,895, filed on Jul. 21, 1999, is hereby claimed.

FIELD OF THE INVENTION

The present invention relates generally to a series of novel small molecules, their synthesis and their use in the treatment of inflammatory disease.

BACKGROUND OF THE INVENTION

Research spanning the last decade has helped to elucidate the molecular events attending cell-cell interactions in the body, especially those events involved in the movement and activation of cells in the immune system. See generally, Springer, T. *Nature*, 1990, 346, 425–434. Cell surface proteins, and especially the Cellular Adhesion Molecules ("CAMs") and "Leukointegrins", including LFA-1, MAC-1 and gp 150.95 (referred to in WHO nomenclature as CD18/CD11 a, CD18/CD 11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117–138 and Diamond, M.; Springer, T. *Current Biology*, 1994, 4, 506–532.

A group of individuals has been identified which lack the appropriate expression of Leukointegrins, a condition termed "Leukocyte Adhesion Deficiency" (Anderson, D. C.; et al., *Fed. Proc.* 1985, 44, 2671–2677 and Anderson, D. C.; et al., *J. Infect. Dis.* 1985, 152, 668–689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today*, 1994, 15, 251–255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1–38, Cosimi, C. B.; et al., *J Immunol.* 1990, 144, 4604–4612 and Kavanaugh, A.; et al., *Arthritis Rheum.* 1994, 37, 992–1004) and antibodies directed against LFA-1 have demonstrated immunosuppressive effects in bone marrow transplantation and in the prevention of early rejection of renal allografts (Fischer, A.; et al., *Lancet*, 1989, 2, 1058–1060 and Le Mauff, B.; et al., *Transplantation*, 1991, 52, 291–295).

It has also been demonstrated that a recombinant soluble form of ICAM-1 can act as an inhibitor of the ICAM-1 interaction with LFA-1. Soluble ICAM-1 acts as a direct antagonist of CD18,CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al, *J. Immunol.* 1993, 151, 7224 and Roep, B. O.; et al., Lancet, 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

Several small molecules have been described in the literature which affect the interaction of CAMs and Leukointegrins. A natural product isolated from the root of *Trichilia rubra* was found to be inhibitory in an in vitro cell binding assay (Musza, L. L.; et al., *Tetrahedron*, 1994, 50, 11369–11378). One series of molecules (Boschelli, D. H.; et al., *J. Med. Chem.* 1994, 37, 717 and Boschelli, D. H.; et al., *J. Med. Chem.* 1995, 38, 4597–4614) was found to be orally active in a reverse passive Arthus reaction, an induced model of inflammation that is characterized by neutrophil accumulation (Chang, Y. H.; et al., *Eur. J. Pharmacol.* 1992, 69, 155–164). Another series of molecules was also found to be orally active in a delayed type hypersensitivity reaction in rats (Sanfilippo, P. J.; et al., *J. Med. Chem.* 1995, 38, 1057–1059). All of these molecules appear to act nonspecifically, either by inhibiting the transcription of ICAM-1 along with other proteins or act intracellularly to inhibit the activation of the Leukointegrins by an unknown mechanism. None of the molecules directly antagonize the interaction of the CAMs with the Leukointegrins. Due to lack of potency, lack of selectivity and lack of a specific mechanism of action, the described small molecules are not likely to be satisfactory for therapeutic use.

It follows that small molecules having the similar ability as large protein molecules to directly and selectively antagonize the binding of the CAMs to the Leukointegrins would make preferable therapeutic agents. WO9839303 discloses a class of small molecule inhibitors of the interaction of LFA-1 and ICAM-1. WO9911258 discloses that the fungal metabolite mevinolin and derivatives bind to LFA-1 and disrupt the interaction of LFA-1 and ICAM-1.

SUMMARY OF THE INVENTION

A first aspect of the invention comprises a method for treating or preventing inflammatory and immune cell-mediated diseases by the administration of certain novel small molecules. These compounds act by inhibiting the interaction of cellular adhesion molecules, specifically by antagonizing the binding of human intercellular adhesion molecules (including ICAM-1, ICAM-2 and ICAM-3) to the Leukointegrins (especially CD18/CD11a). A second aspect of the invention comprises novel small molecules having the above-noted therapeutic activities. A third aspect of the invention comprises methods for making these novel compounds. A final aspect of the invention comprises pharmaceutical compositions comprising the above-mentioned compounds suitable for the prevention or treatment of inflammatory and immune cell-mediated conditions.

DETAILED DESCRIPTION OF THE INVENTION

The invention comprises compounds of the formula I:

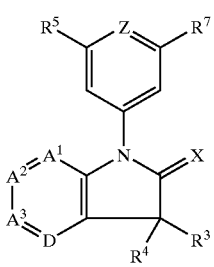

(I)

wherein:
$A^1$, $A^2$ and $A^3$ are each, independently, =N— or =CH—;
D is =N—, =CR$^1$—, =CSO$_2$R$^1$—, =CSOR$^1$—, =CSR$^1$—, =COR$^1$—, =CCOR$^1$—, or =CNHR$^1$—,
wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be mono- or polysubstituted with:
(i) halogen,
(ii) oxo,
(iii) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridi-
nyl and quinazolinyl, wherein one or more hydrogen atoms of said aryl group may be optionally and independently replaced with:
(a) alkyl of 1 to 3 carbon atoms,
(b) —COOH,
(c) —SO$_2$OH,
(d) —PO(OH)$_2$,
(e) a group of the formula —COOR$^8$, wherein $R^8$ is straight or branched alkyl of 1 to 5 carbon atoms or cycloalkyl of 3 to 5 carbon atoms,
(f) a group of the formula —NR$^9$R$^{10}$, wherein $R^9$ and $R^{10}$ are each independently a hydrogen atom, alkyl of 1 to 6 carbon atoms, cycloalkyl of 3 to 6 carbon atoms or acyl of 1 to 7 carbon atoms, or wherein $R^9$ and $R^{10}$ constitute a saturated hydrocarbon bridge of 3 to 5 carbon atoms which together with the nitrogen atom between them form a heterocyclic ring,
(g) a group of the formula —CONR$^{11}$R$^{12}$, wherein $R^{11}$ and $R^{12}$ are each independently a hydrogen atom, alkyl of 1 to 6 carbon atoms or cycloalkyl of 3 to 6 carbon atoms, or wherein $R^{11}$ and $R^{12}$ constitute a saturated hydrocarbon bridge of 3 to 5 carbon atoms which together with the nitrogen atom between them form a heterocyclic ring,
(h) a group of the formula —OR$^{13}$, wherein $R^{13}$ is a hydrogen atom, or an alkyl or acyl group of 1 to 7 carbon atoms,
(i) a group of the formula —SR$^{14}$, wherein $R^{14}$ is a hydrogen atom, or an alkyl or acyl group of 1 to 7 carbon atoms,
(j) cyano, or
(k) an amidino group of the formula:

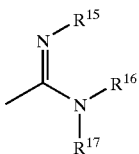

wherein $R^{15}$, $R^{16}$ and $R^{17}$ are each, independently, a hydrogen atom or alkyl of 1 to 3 carbon atoms and wherein two of $R^{15}$, $R^{16}$ and $R^{17}$ may additionally constitute a saturated hydrocarbon bridge of 3 to 5 carbon atoms which together with the nitrogen atom(s) between them form a heterocyclic ring,
(iv) a group of the formula —COOR$^{18}$, wherein $R^{18}$ is straight or branched alkyl of 1 to 7 carbon atoms or cycloalkyl of 3 to 6 carbon atoms,
(v) cyano,
(vi) a group of the formula —CONR$^{19}$R$^{20}$, wherein $R^{19}$ and $R^{20}$ are each, independently, a hydrogen atom, alkyl of 1 to 6 carbon atoms or cycloalkyl of 3 to 6 carbon atoms, or wherein $R^{19}$ and $R^{20}$ constitute a saturated hydrocarbon bridge of 3 to 5 carbon atoms which together with the nitrogen atom between them form a heterocyclic ring,
(vii) a group of the formula —OR$^{21}$, wherein $R^{21}$ is a hydrogen atom, or an alkyl or acyl group of 1 to 7 carbon atoms,
(viii) a group of the formula —SR$^{22}$, wherein $R^{22}$ is a hydrogen atom, or an alkyl or acyl group of 1 to 7 carbon atoms,
(ix) a group of the formula —NR$^{23}$R$^{24}$, wherein $R^{23}$ and $R^{24}$ are each, independently, (a) a hydrogen atom,
(b) alkyl or acyl of 1 to 7 carbon atoms or cycloalkyl of 3 to 7 carbon atoms,
(c) a group of the formula —$(CH_2)_m$COOH, wherein m is 0, 1 or 2, or
(d) a group of the formula —$(CH_2)_n$COOR$^{25}$, wherein n is 0, 1 or 2, wherein R$^{25}$ is straight or branched alkyl of 1 to 6 carbon atoms,
or wherein R$^{23}$ and R$^{24}$ constitute a saturated hydrocarbon bridge of 3 to 5 carbon atoms which together with the nitrogen atom between them form a heterocyclic ring, or
(x) a quaternary group of the formula:

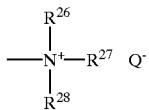

wherein R$^{26}$, R$^{27}$ and R$^{28}$ are each, independently, a branched or unbranched alkyl group of 1 to 7 carbon atoms and Q$^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula:

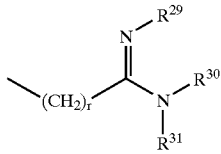

wherein r is 2, 3, 4, 5 or 6, and
R$^{29}$, R$^{30}$ and R$^{31}$ are each, independently, a hydrogen atom or alkyl of 1 to 3 carbon atoms, and wherein two of R$^{29}$, R$^{30}$ and R$^{31}$ may additionally constitute a saturated hydrocarbon bridge of 3 to 5 carbon atoms which together with the nitrogen atom(s) between them form a heterocyclic ring,
(G) an guanidino group of the formula:

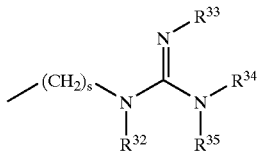

wherein s is 2, 3, 4, 5 or 6, and
R$^{32}$, R$^{33}$, R$^{34}$ and R$^{35}$ are each, independently, a hydrogen atom or alkyl of 1 to 3 carbon atoms, and wherein two of R$^{32}$, R$^{33}$, R$^{34}$ and R$^{35}$ may additionally constitute a saturated hydrocarbon bridge of 3 to 5 carbon atoms which together with the nitrogen atom(s) between them form a heterocyclic ring,
(H) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
(i) alkyl of 1 to 3 carbon atoms,
(ii) —COOH,
(iii) —SO$_2$OH,
(iv) —PO(OH)$_2$,
(v) a group of the formula —COOR$^{36}$, wherein R$^{36}$ is straight or branched alkyl of 1 to 5 carbon atoms or cycloalkyl of 3 to 5 carbon atoms,
(vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring,
(vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring,
(viii) a group of the formula —OR$^{41}$, wherein R$^{41}$ is a hydrogen atom, or an alkyl or acyl group of 1 to 7 carbon atoms,
(ix) a group of the formula —SR$^{42}$, wherein R$^{42}$ is a hydrogen atom, or an alkyl or acyl group of 1 to 7 carbon atoms,
(x) cyano, or
(xi) an amidino group of the formula:

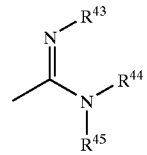

wherein R$^{43}$, R$^{44}$ and R$^{45}$ are each, independently, a hydrogen atom or alkyl of 1 to 3 carbon atoms, and wherein two of R$^{43}$, R$^{44}$ and R$^{45}$ may additionally constitute a saturated hydrocarbon bridge of 3 to 5 carbon atoms which together with the nitrogen atom(s) between them form a heterocyclic ring,
(I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ constitute a saturated hydrocarbon bridge of 3 to 5 carbon atoms which together with the nitrogen atom between them form a heterocyclic ring,
(J) a morpholinyl moiety, or,
(K) halogen;
X is an oxygen or sulfur atom;
R$^3$ is:
(A) a hydrogen atom, or
(B) branched or unbranched alkyl of 1 to 3 carbon atoms or cycloalkyl of 3 to 5 carbon atoms wherein said alkyl or cycloalkyl group may optionally be substituted with:

(i) a group of the formula —OR$^{48}$, wherein R$^{48}$ is a hydrogen atom, or an alkyl or acyl group of 1 to 7 carbon atoms, or (ii) a group of the formula —NR$^{49}$R$^{50}$, wherein R$^{49}$ and R$^{50}$ are each, independently, a hydrogen atom, alkyl of 1 to 2 carbon atoms, or acyl of 1 to 2 carbon atoms;

R$^4$ is a group of the formula —(CR$^{51}$R$^{52}$)$_x$(CR$^{53}$R$^{54}$)$_y$R$^{55}$, wherein;

x and y are each independently 0 or 1,

R$^{51}$, R$^{52}$ and R$^{53}$ are each, independently:

(A) a hydrogen atom, (B) a group of the formula —OR$^{56}$, wherein R$^{56}$ is a hydrogen atom, or an alkyl or acyl group of 1 to 7 carbon atoms, or (C) branched or unbranched alkyl of 1 to 3 carbon atoms or cycloalkyl of 3 to 5 carbon atoms, R$^{54}$ is:

(A) a group of the formula R$^{57}$, wherein R$^{57}$ is defined similarly to R$^1$ above, or (B) a group of the formula —OR$^{58}$, wherein R$^{58}$ is defined similarly to R$^1$ above;

R$^{55}$ is:

aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:

(A) R$^{59}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:

(i) branched or unbranched alkyl of 1 to 6 carbon atoms or cycloalkyl of 3 to 6 carbon atoms, which alkyl or cycloakyl group may be mono- or polysubstituted with halogen or oxo, (ii) a group of the formula —COOR$^{60}$, wherein R$^{60}$ is straight or branched alkyl of 1 to 5 carbon atoms or cycloalkyl of 3 to 5 carbon atoms, (iii) a group of the formula —NR$^{61}$R$^{62}$, wherein R$^{61}$ and R$^{62}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{61}$ and R$^{62}$ constitute a saturated hydrocarbon bridge of 3 to 5 carbon atoms which together with the nitrogen atom between them form a heterocyclic ring, (iv) a group of the formula —CONR$^{63}$R$^{64}$, wherein R$^{63}$ and R$^{64}$ are each, independently, a hydrogen atom, alkyl or fluoroalkyl of 1 to 6 carbon atoms or cycloalkyl of 3 to 6 carbon atoms, or wherein R$^{63}$ and R$^{64}$ constitute a saturated hydrocarbon bridge of 3 to 5 carbon atoms which together with the nitrogen atom between them form a heterocyclic ring, (v) a group of the formula —OR$^{65}$, wherein R$^{65}$ is a hydrogen atom, or an alkyl, fluoroalkyl or acyl group of 1 to 7 carbon atoms, (vi) a group of the formula —SR$^{66}$, wherein R$^{66}$ is a hydrogen atom, or an alkyl, fluoroalkyl or acyl group of 1 to 7 carbon atoms, (vii) cyano, (viii) nitro, or (ix) halogen, (B) methyl, which may be mono- or polysubstituted with fluorine atoms and additionally may be monosubstituted with R$^{59}$, (C) branched or unbranched alkyl of 2 to 6 carbon atoms or cycloalkyl of 3 to 6 carbon atoms, which alkyl or cycloakyl group may be mono- or polysubstituted with halogen or oxo, (D) a group of the formula —COOR$^{67}$, wherein R$^{67}$ is straight or branched alkyl of 1 to 5 carbon atoms or cycloalkyl of 3 to 5 carbon atoms, (E) a group of the formula —NR$^{68}$R$^{69}$, wherein R$^{68}$ and R$^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{68}$ and R$^{69}$ constitute a saturated hydrocarbon bridge of 3 to 5 carbon atoms which together with the nitrogen atom between them form a heterocyclic ring, and wherein one of R$^{68}$ and R$^{69}$ may additionally be the group R$^{59}$, (F) a group of the formula —CONR$^{70}$R$^{71}$, wherein R$^{70}$ and R$^{71}$ are each, independently, a hydrogen atom, alkyl or fluoroalkyl of 1 to 6 carbon atoms or cycloalkyl of 3 to 6 carbon atoms, or wherein R$^{70}$ and R$^{71}$ constitute a saturated hydrocarbon bridge of 3 to 5 carbon atoms which together with the nitrogen atom between them form a heterocyclic ring, and wherein one of R$^{70}$ and R$^{71}$ may additionally be the group R$^{59}$, (G) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$, (H) a group of the formula —OR$^{73}$, wherein R$^{73}$ is a hydrogen atom, an alkyl, fluoroalkyl or acyl group of 1 to 7 carbon atoms, or R$^{59}$, (I) a group of the formula —SR$^{74}$, wherein R$^{74}$ is a hydrogen atom, an alkyl, fluoroalkyl or acyl group of 1 to 7 carbon atoms, or R$^{59}$, (J) cyano,
(K) nitro, or
(L) halogen;

$R^5$ is Cl or trifluoromethyl;

Z is =N— or =CR$^6$— wherein $R^6$ is a hydrogen, fluorine, chlorine, bromine or iodine atom, methyl or trifluoromethyl; and, $R^7$ is a hydrogen, fluorine, chlorine, bromine or iodine atom, methyl, cyano, nitro or trifluoromethyl, with the condition that when Z is N or =CH—, $R^7$ is chlorine or trufluoromethyl;

and pharmaceutically acceptable salts thereof

As the term is used herein, a "pharmaceutically acceptable counter ion" is any counter ion generally regarded by those skilled in the pharmaceutical art as being pharmaceutically acceptable. For a discussion of what are pharmaceutically acceptable counter ions, reference may be had to Stephen M. Bergle, Lyle D. Bighley and Donald C. Monkhouse, "Pharmaceutical Salts", *Journal of Pharmaceutical Sciences*, 66 (1977), 1–19. By way of non-limiting example, the chloride, bromide, acetate, and sulphate ions are pharmaceutically acceptable counter ions.

Preferred compounds of the invention are those of formula I as given above wherein:

$A^1$, $A^2$ and $A^3$ are each, independently, =N— or =CH—;
D is =N—, =CR$^1$—, =CSO$_2$R$^1$—, =CSOR$^1$—, =CSR$^1$—, =COR$^1$—, =CCOR$^1$—, or =CNHR$^1$—,
wherein $R^1$ is:

(A) a hydrogen atom,
(B) branched or unbranched alkyl of 1 to 6 carbon atoms or cycloalkyl of 3 to 6 carbon atoms, which alkyl or cycloakyl group may be mono- or polysubstituted with:
  (i) halogen,
  (ii) oxo,
  (iii) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
    (a) alkyl of 1 to 3 carbon atoms,
    (b) —COOH,
    (c) —SO$_2$OH,
    (d) —PO(OH)$_2$,
    (e) a group of the formula —COOR$^8$, wherein $R^8$ is straight or branched alkyl of 1 to 5 carbon atoms or cycloalkyl of 3 to 5 carbon atoms,
    (f) a group of the formula —NR$^9$R$^{10}$, wherein $R^9$ and $R^{10}$ are each independently a hydrogen atom, alkyl of 1 to 6 carbon atoms, cycloalkyl of 3 to 6 carbon atoms or acyl of 1 to 7 carbon atoms, or wherein $R^9$ and $R^{10}$ constitute a saturated hydrocarbon bridge of 3 to 5 carbon atoms which together with the nitrogen atom between them form a heterocyclic ring,
    (g) a group of the formula —CONR$^{11}$R$^{12}$, wherein $R^{11}$ and $R^{12}$ are each independently a hydrogen atom, alkyl of 1 to 6 carbon atoms or cycloalkyl of 3 to 6 carbon atoms, or wherein $R^{11}$ and $R^{12}$ constitute a saturated hydrocarbon bridge of 3 to 5 carbon atoms which together with the nitrogen atom between them form a heterocyclic ring,
    (h) a group of the formula —OR$^{13}$, wherein $R^{13}$ is a hydrogen atom, or an alkyl or acyl group of 1 to 7 carbon atoms,
    (i) a group of the formula —SR$^{14}$, wherein $R^{14}$ is a hydrogen atom, or an alkyl or acyl group of 1 to 7 carbon atoms,
    (j) cyano, or
    (k) an amidino group of the formula:

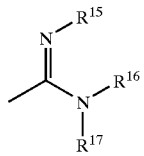

wherein $R^{15}$, $R^{16}$ and $R^{17}$ are each, independently, a hydrogen atom or alkyl of 1 to 3 carbon atoms and wherein two of $R^{15}$, $R^{16}$ and $R^{17}$ may additionally constitute a saturated hydrocarbon bridge of 3 to 5 carbon atoms which together with the nitrogen atom(s) between them form a heterocyclic ring,
    (iv) a group of the formula —COOR$^{18}$, wherein $R^{18}$ is straight or branched alkyl of 1 to 7 carbon atoms or cycloalkyl of 3 to 6 carbon atoms,
    (v) cyano,
    (vi) a group of the formula —CONR$^{19}$R$^{20}$, wherein $R^{19}$ and $R^{20}$ are each, independently, a hydrogen atom, alkyl of 1 to 6 carbon atoms or cycloalkyl of 3 to 6 carbon atoms, or wherein $R^{19}$ and $R^{20}$ constitute a saturated hydrocarbon bridge of 3 to 5 carbon atoms which together with the nitrogen atom between them form a heterocyclic ring,
    (vii) a group of the formula —OR$^{21}$, wherein $R^{21}$ is a hydrogen atom, or an alkyl or acyl group of 1 to 7 carbon atoms,
    (viii) a group of the formula —SR$^{22}$, wherein $R^{22}$ is a hydrogen atom, or an alkyl or acyl group of 1 to 7 carbon atoms,
    (ix) a group of the formula —NR$^{23}$R$^{24}$, wherein $R^{23}$ and $R^{24}$ are each, independently,
      (a) a hydrogen atom,
      (b) alkyl or acyl of 1 to 7 carbon atoms or cycloalkyl of 3 to 7 carbon atoms,
      (c) a group of the formula —(CH$_2$)$_m$COOH, wherein m is 0, 1 or 2, or
      (d) a group of the formula —(CH$_2$)$_n$COOR$^{25}$, wherein n is 0, 1 or 2, wherein $R^{25}$ is straight or branched alkyl of 1 to 6 carbon atoms,
    or wherein $R^{23}$ and $R^{24}$ constitute a saturated hydrocarbon bridge of 3 to 5 carbon atoms which together with the nitrogen atom between them form a heterocyclic ring, or
    (x) a quaternary group of the formula:

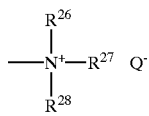

wherein $R^{26}$, $R^{27}$ and $R^{28}$ are each, independently, a branched or unbranched alkyl group of 1 to 7 carbon atoms and $Q^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

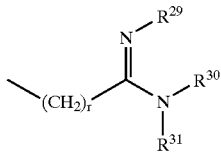

wherein r is 2, 3, 4, 5 or 6, and
$R^{29}$, $R^{30}$ and $R^{31}$ are each, independently, a hydrogen atom or alkyl of 1 to 3 carbon atoms, and wherein two of $R^{29}$, $R^{30}$ and $R^{31}$ may additionally constitute a saturated hydrocarbon bridge of 3 to 5 carbon atoms which together with the nitrogen atom(s) between them form a heterocyclic ring, (G) an guanidino group of the formula:

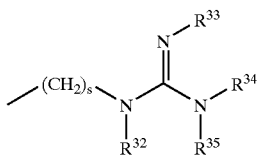

wherein s is 2, 3, 4, 5 or 6, and
$R^{32}$, $R^{33}$, $R^{34}$ and $R^{35}$ are each, independently, a hydrogen atom or alkyl of 1 to 3 carbon atoms, and wherein two of $R^{32}$, $R^{33}$, $R^{34}$ and $R^{35}$ may additionally constitute a saturated hydrocarbon bridge of 3 to 5 carbon atoms which together with the nitrogen atom(s) between them form a heterocyclic ring, (H) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group may be optionally and independently replaced with:
 (i) alkyl of 1 to 3 carbon atoms,
 (ii) —COOH,
 (iii) —$SO_2OH$,
 (iv) —$PO(OH)_2$,
 (v) a group of the formula —$COOR^{36}$, wherein $R^{36}$ is straight or branched alkyl of 1 to 5 carbon atoms or cycloalkyl of 3 to 5 carbon atoms,
 (vi) a group of the formula —$NR^{37}R^{38}$, wherein $R^{37}$ and $R^{38}$ are each, independently, a hydrogen atom, alkyl of 1 to 6 carbon atoms, cycloalkyl of 3 to 6 carbon atoms or acyl of 1 to 7 carbon atoms, or wherein $R^{37}$ and $R^{38}$ constitute a saturated hydrocarbon bridge of 3 to 5 carbon atoms which together with the nitrogen atom between them form a heterocyclic ring,
 (vii) a group of the formula —$CONR^{39}R^{40}$, wherein $R^{39}$ and $R^{40}$ are each, independently, a hydrogen atom, alkyl of 1 to 6 carbon atoms or cycloalkyl of 3 to 6 carbon atoms, or wherein $R^{39}$ and $R^{40}$ constitute a saturated hydrocarbon bridge of 3 to 5 carbon atoms which together with the nitrogen atom between them form a heterocyclic ring,
 (viii) a group of the formula —$OR^{41}$, wherein $R^{41}$ is a hydrogen atom, or an alkyl or acyl group of 1 to 7 carbon atoms,
 (ix) a group of the formula —$SR^{42}$, wherein $R^{42}$ is a hydrogen atom, or an alkyl or acyl group of 1 to 7 carbon atoms,
 (x) cyano, or
 (xi) an amidino group of the formula:

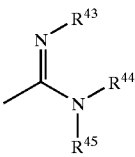

wherein $R^{43}$, $R^{44}$ and $R^{45}$ are each, independently, a hydrogen atom or alkyl of 1 to 3 carbon atoms, and wherein two of $R^{43}$, $R^{44}$ and $R^{45}$ may additionally constitute a saturated hydrocarbon bridge of 3 to 5 carbon atoms which together with the nitrogen atom(s) between them form a heterocyclic ring, (I) a group of the formula —$NR^{46}R^{47}$, wherein $R^{46}$ and $R^{47}$ are each independently a hydrogen atom, alkyl of 1 to 6 carbon atoms, cycloalkyl of 3 to 6 carbon atoms or acyl of 1 to 7 carbon atoms, or wherein $R^{46}$ and $R^{47}$ constitute a saturated hydrocarbon bridge of 3 to 5 carbon atoms which together with the nitrogen atom between them form a heterocyclic ring, (J) a morpholinyl moiety, or, (K) halogen;

X is an oxygen or sulfur atom;

$R^3$ is:
 (A) a hydrogen atom, or
 (B) branched or unbranched alkyl of 1 to 3 carbon atoms or cycloalkyl of 3 to 5 carbon atoms wherein said alkyl or cycloalkyl group may optionally be substituted with:
  (i) a group of the formula —$OR^{48}$, wherein $R^{48}$ is a hydrogen atom, or an alkyl or acyl group of 1 to 7 carbon atoms, or
  (ii) a group of the formula —$NR^{49}R^{50}$, wherein $R^{49}$ and $R^{50}$ are each, independently, a hydrogen atom, alkyl of 1 to 2 carbon atoms, or acyl of 1 to 2 carbon atoms;

$R^4$ is a group of the formula —$CH_2R^{55}$, wherein:
 $R^{55}$ is:
  aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:

(A) $R^{59}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, -3, 6- or 7-indolyzinyl, 2-, 3-, 5- or 6-isoindolyl, 2-, 3-, 5- or 6-benzo[b] furanyl, 2-, 3-, 5- or 6-benzo[b] thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group may be optionally and independently replaced with:
  (i) branched or unbranched alkyl of 1 to 6 carbon atoms or cycloalkyl of 3 to 6 carbon atoms, which alkyl or cycloakyl group may be mono- or polysubstituted with halogen or oxo,
  (ii) cyano,
  (iii) nitro, or
  (iv) halogen,
(B) methyl, which may be mono- or polysubstituted with fluorine atoms and additionally may be monosubstituted with $R^{59}$,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{67}$, wherein $R^{67}$ is straight or branched alkyl of 1 to 5 carbon atoms or cycloalkyl of 3 to 5 carbon atoms,
(E) a group of the formula —$NR^{68}R^{69}$, wherein $R^{68}$ and $R^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{68}$ and $R^{69}$ constitute a saturated hydrocarbon bridge of 3 to 5 carbon atoms which together with the nitrogen atom between them form a heterocyclic ring, and wherein one of $R^{68}$ and $R^{69}$ may additionally be the group $R^{59}$,
(F) a group of the formula $CONR^{70}R^{71}$, wherein $R^{70}$ and $R^{71}$ are each, independently, a hydrogen atom, alkyl or fluoroalkyl of 1 to 6 carbon atoms or cycloalkyl of 3 to 6 carbon atoms, or wherein $R^{70}$ and $R^{71}$ constitute a saturated hydrocarbon bridge of 3 to 5 carbon atoms which together with the nitrogen atom between them form a heterocyclic ring, and wherein one of $R^{70}$ and $R^{71}$ may additionally be the group $R^{59}$,
(G) a group of the formula —$COR^{72}$, wherein $R^{72}$ is a hydrogen atom, straight or branched alkyl of 1 to 5 carbon atoms, cycloalkyl of 3 to 5 carbon atoms or $R^{59}$,
(H) a group of the formula —$OR^{73}$, wherein $R^{73}$ is a hydrogen atom, an alkyl, fluoroalkyl or acyl group of 1 to 7 carbon atoms, or $R^{59}$,
(I) a group of the formula —$SR^{74}$, wherein $R^{74}$ is a hydrogen atom, an alkyl, fluoroalkyl or acyl group of 1 to 7 carbon atoms, or $R^{59}$,
(J) cyano,
(K) nitro, or
(L) halogen;

$R^5$ is Cl or trifluoromethyl;

Z is =N— or =$CR^6$— wherein $R^6$ is a hydrogen, fluorine, chlorine, bromine or iodine atom, methyl or trifluoromethyl; and, $R^7$ is a hydrogen, fluorine, chlorine, bromine or iodine atom, methyl, cyano, nitro or trifluoromethyl, with the condition that when Z is N or =CH—, $R^7$ is chlorine or trufluoromethyl;

and pharmaceutically acceptable salts thereof.

More preferred compounds of the invention are those of the formula I, wherein:

$A^1$, $A^2$ and $A^3$ are each, independently, =N— or =CH—;

D is =N—, =$CR^1$—, =$COR^1$—, =$CCOR^1$—, or =$CSO_2R^1$—, wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be mono- or polysubstituted with:
  (i) oxo,
  (ii) phenyl, wherein one or more hydrogen atoms of said phenyl group may be optionally and independently replaced with:
    (a) alkyl of 1 to 3 carbon atoms,
    (b) —COOH,
    (c) —$SO_2OH$,
    (d) —$PO(OH)_2$,
    (e) a group of the formula —$COOR^8$, wherein $R^8$ is straight or branched alkyl of 1 to 5 carbon atoms or cycloalkyl of 3 to 5 carbon atoms,
    (f) a group of the formula —$NR^9R^{10}$, wherein $R^9$ and $R^{10}$ are each independently a hydrogen atom, alkyl of 1 to 6 carbon atoms, cycloalkyl of 3 to 6 carbon atoms or acyl of 1 to 7 carbon atoms, or wherein $R^9$ and $R^{10}$ constitute a saturated hydrocarbon bridge of 3 to 5 carbon atoms which together with the nitrogen atom between them form a heterocyclic ring,
    (g) a group of the formula —$CONR^{11}R^{12}$, wherein $R^{11}$ and $R^{12}$ are each independently a hydrogen atom, alkyl of 1 to 6 carbon atoms or cycloalkyl of 3 to 6 carbon atoms, or wherein $R^{11}$ and $R^{12}$ constitute a saturated hydrocarbon bridge of 3 to 5 carbon atoms which together with the nitrogen atom between them form a heterocyclic ring,
    (h) a group of the formula —$OR^{13}$, wherein $R^{13}$ is a hydrogen atom, or an alkyl or acyl group of 1 to 7 carbon atoms,
    (i) a group of the formula —$SR^{14}$, wherein $R^{14}$ is a hydrogen atom, or an alkyl or acyl group of 1 to 7 carbon atoms,
    (j) cyano, or (k) an amidino group of the formula:

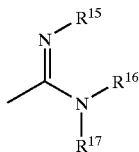

wherein $R^{15}$, $R^{16}$ and $R^{17}$ are each, independently, a hydrogen atom or alkyl of 1 to 3 carbon atoms and wherein two of $R^{15}$, $R^{16}$ and $R^{17}$ may additionally constitute a saturated hydrocarbon bridge of 3 to 5 carbon atoms which together with the nitrogen atom(s) between them form a heterocyclic ring, (iii) a group of the formula —COOR$^{18}$, wherein $R^{18}$ is straight or branched alkyl of 1 to 7 carbon atoms or cycloalkyl of 3 to 6 carbon atoms, (iv) a group of the formula —CONR$^{19}$R$^{20}$, wherein $R^{19}$ and $R^{20}$ are each, independently, a hydrogen atom, alkyl of 1 to 6 carbon atoms or cycloalkyl of 3 to 6 carbon atoms, or wherein $R^{19}$ and $R^{20}$ constitute a saturated hydrocarbon bridge of 3 to 5 carbon atoms which together with the nitrogen atom between them form a heterocyclic ring, (v) a group of the formula —OR$^{21}$, wherein $R^{21}$ is a hydrogen atom, or an alkyl or acyl group of 1 to 7 carbon atoms, (vi) a group of the formula —NR$^{23}$R$^{24}$, wherein $R^{23}$ and $R^{24}$ are each, independently,
  (a) a hydrogen atom,
  (b) alkyl or acyl of 1 to 7 carbon atoms or cycloalkyl of 3 to 7 carbon atoms,
  (c) a group of the formula —(CH$_2$)$_m$COOH, wherein m is 0, 1 or 2, or
  (d) a group of the formula —(CH$_2$)$_n$COOR$^{25}$, wherein n is 0, 1 or 2, wherein $R^{25}$ is straight or branched alkyl of 1 to 6 carbon atoms,
  or wherein $R^{23}$ and $R^{24}$ constitute a saturated hydrocarbon bridge of 3 to 5 carbon atoms which together with the nitrogen atom between them form a heterocyclic ring, or (vii) a quaternary group of the formula:

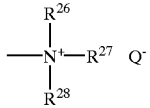

wherein $R^{26}$, $R^{27}$ and $R^{28}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

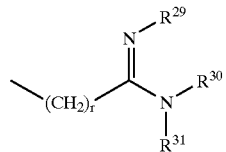

wherein r is 2, 3, 4, 5 or 6, and
$R^{29}$, $R^{30}$ and $R^{31}$ are each, independently, a hydrogen atom or alkyl of 1 to 3 carbon atoms, and wherein two of $R^{29}$, $R^{30}$ and $R^{31}$ may additionally constitute a saturated hydrocarbon bridge of 3 to 5 carbon atoms which together with the nitrogen atom(s) between them form a heterocyclic ring, (G) an guanidino group of the formula:

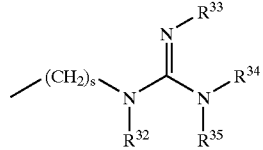

wherein s is 2, 3, 4, 5 or 6, and
$R^{32}$, $R^{33}$, $R^{34}$ and $R^{35}$ are each, independently, a hydrogen atom or alkyl of 1 to 3 carbon atoms, and wherein two of $R^{32}$, $R^{33}$, $R^{34}$ and $R^{35}$ may additionally constitute a saturated hydrocarbon bridge of 3 to 5 carbon atoms which together with the nitrogen atom(s) between them form a heterocyclic ring, (H) phenyl, wherein one or more hydrogen atoms of said phenyl group may be optionally and independently replaced with:
  (i) alkyl of 1 to 3 carbon atoms,
  (ii) —COOH,
  (iii) —SO$_2$OH,
  (iv) —PO(OH)$_2$,
  (v) a group of the formula —COOR$^{36}$, wherein $R^{36}$ is straight or branched alkyl of 1 to 5 carbon atoms or cycloalkyl of 3 to 5 carbon atoms,
  (vi) a group of the formula —NR$^{37}$R$^{38}$, wherein $R^{37}$ and $R^{38}$ are each, independently, a hydrogen atom, alkyl of 1 to 6 carbon atoms, cycloalkyl of 3 to 6 carbon atoms or acyl of 1 to 7 carbon atoms, or wherein $R^{37}$ and $R^{38}$ constitute a saturated hydrocarbon bridge of 3 to 5 carbon atoms which together with the nitrogen atom between them form a heterocyclic ring,
  (vii) a group of the formula —CONR$^{39}$R$^{40}$, wherein $R^{39}$ and $R^{40}$ are each, independently, a hydrogen atom, alkyl of 1 to 6 carbon atoms or cycloalkyl of 3 to 6 carbon atoms, or wherein $R^{39}$ and $R^{40}$ constitute a saturated hydrocarbon bridge of 3 to 5 carbon atoms which together with the nitrogen atom between them form a heterocyclic ring,
  (viii) a group of the formula —OR$^{41}$, wherein $R^{41}$ is a hydrogen atom, or an alkyl or acyl group of 1 to 7 carbon atoms,
  (ix) a group of the formula —SR$^{42}$, wherein $R^{42}$ is a hydrogen atom, or an alkyl or acyl group of 1 to 7 carbon atoms,
  (x) cyano, or (xi) an amidino group of the formula:

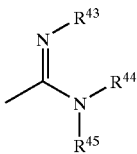

wherein $R^{43}$, $R^{44}$ and $R^{45}$ are each, independently, a hydrogen atom or alkyl of 1 to 3 carbon atoms, and wherein two of $R^{43}$, $R^{44}$ and $R^{45}$ may additionally constitute a saturated hydrocarbon bridge of 3 to 5 carbon atoms which together with the nitrogen atom(s) between them form a heterocyclic ring,
(I) a group of the formula —$NR^{46}R^{47}$, wherein $R^{46}$ and $R^{47}$ are each independently a hydrogen atom, alkyl of 1 to 6 carbon atoms, cycloalkyl of 3 to 6 carbon atoms or acyl of 1 to 7 carbon atoms, or wherein $R^{46}$ and $R^{47}$ constitute a saturated hydrocarbon bridge of 3 to 5 carbon atoms which together with the nitrogen atom between them form a heterocyclic ring,
(J) a morpholinyl moiety, or,
(K) halogen;
X is an oxygen atom;
$R^3$ is:
(A) branched or unbranched alkyl of 1 to 3 carbon atoms or cycloalkyl of 3 to 5 carbon atoms;
$R^4$ is a group of the formula —$CH_2R^{55}$, wherein;
$R^{55}$ is:
phenyl, wherein one or more of the hydrogen atoms at the 3 and 4 positions of said phenyl group may be optionally and independently replaced with:
(A) $R^{59}$, which is aryl selected from the class consisting of phenyl, 2-, 3- or 4-pyridyl, or 2-, 4- or 5-pyrimidinyl, wherein one or more of the hydrogen atoms of said aryl group may be optionally and independently replaced with:
(i) branched or unbranched alkyl of 1 to 6 carbon atoms or cycloalkyl of 3 to 6 carbon atoms, which alkyl or cycloakyl group may be mono- or polysubstituted with halogen or oxo,
(ii) cyano,
(iii) nitro, or
(iv) halogen,
(B) methyl,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{67}$, wherein $R^{67}$ is straight or branched alkyl of 1 to 5 carbon atoms or cycloalkyl of 3 to 5 carbon atoms,
(E) a group of the formula —$COR^{72}$, wherein $R^{72}$ is a hydrogen atom, straight or branched alkyl of 1 to 5 carbon atoms, cycloalkyl of 3 to 5 carbon atoms or $R^{59}$,
(F) a group of the formula —$OR^{73}$, wherein $R^{73}$ is a hydrogen atom, an alkyl , fluoroalkyl or acyl group of 1 to 7 carbon atoms, or $R^{59}$,
(G) a group of the formula —$SR^{74}$, wherein $R^{74}$ is a hydrogen atom, an alkyl , fluoroalkyl or acyl group of 1 to 7 carbon atoms, or $R^{59}$,
(H) cyano,
(I) nitro, or
(J) halogen;

$R^5$ is Cl;
Z is =CH—; and,
$R^7$ is Cl;
and pharmaceutically acceptable salts thereof.
Even more preferred compounds are those of the formula I, wherein:
$A^1$, $A^2$ and $A^3$ are each =CH—;
D is =$CR^1$—, =$COR^1$—, =$CCOR^1$—, or =$CSO_2R^1$—, wherein $R^1$ is:
(A) a hydrogen atom,
(B) branched or unbranched alkyl of 1 to 6 carbon atoms or cycloalkyl of 3 to 6 carbon atoms, which alkyl or cycloakyl group may be mono- or polysubstituted with:
(i) oxo,
(ii) phenyl, wherein one or more hydrogen atoms of said phenyl group may be optionally and independently replaced with:
(a) alkyl of 1 to 3 carbon atoms,
(b) —COOH,
(c) —$SO_2OH$,
(d) —$PO(OH)_2$,
(e) a group of the formula —$COOR^8$, wherein $R^8$ is straight or branched alkyl of 1 to 5 carbon atoms or cycloalkyl of 3 to 5 carbon atoms,
(f) a group of the formula —$NR^9R^{10}$, wherein $R^9$ and $R^{10}$ are each independently a hydrogen atom, alkyl of 1 to 6 carbon atoms, cycloalkyl of 3 to 6 carbon atoms or acyl of 1 to 7 carbon atoms, or wherein $R^9$ and $R^{10}$ constitute a saturated hydrocarbon bridge of 3 to 5 carbon atoms which together with the nitrogen atom between them form a heterocyclic ring,
(g) a group of the formula —$CONR^{11}R^{12}$, wherein $R^{11}$ and $R^{12}$ are each independently a hydrogen atom, alkyl of 1 to 6 carbon atoms or cycloalkyl of 3 to 6 carbon atoms, or wherein $R^{11}$ and $R^{12}$ constitute a saturated hydrocarbon bridge of 3 to 5 carbon atoms which together with the nitrogen atom between them form a heterocyclic ring,
(h) a group of the formula —$OR^{13}$, wherein $R^{13}$ is a hydrogen atom, or an alkyl or acyl group of 1 to 7 carbon atoms,
(i) a group of the formula —$SR^{14}$, wherein $R^{14}$ is a hydrogen atom, or an alkyl or acyl group of 1 to 7 carbon atoms,
(j) cyano, or
(k) an amidino group of the formula:

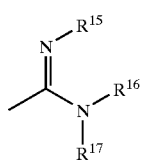

wherein $R^{15}$, $R^{16}$ and $R^{17}$ are each, independently, a hydrogen atom or alkyl of 1 to 3 carbon atoms and wherein two of $R^{15}$, $R^{16}$ and $R^{17}$ may additionally constitute a saturated hydrocarbon bridge of 3 to 5 carbon atoms which together with the nitrogen atom(s) between them form a heterocyclic ring,
(iii) a group of the formula —$COOR^{18}$, wherein $R^{18}$ is straight or branched alkyl of 1 to 7 carbon atoms or cycloalkyl of 3 to 6 carbon atoms, (iv) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, (v) a group of the formula —OR$^{21}$, wherein R$^{21}$ is a hydrogen atom, or an alkyl or acyl group of 1 to 7 carbon atoms, (vi) a group of the formula —NR$^{23}$R$^{24}$, wherein R$^{23}$ and R$^{24}$ are each, independently,
  (a) a hydrogen atom,
  (b) alkyl or acyl of 1 to 7 carbon atoms or cycloalkyl of 3 to 7 carbon atoms,
  (c) a group of the formula —(CH$_2$)$_m$COOH, wherein m is 0, 1 or 2, or
  (d) a group of the formula —(CH$_2$)$_n$COOR$^{25}$, wherein n is 0, 1 or 2, wherein R$^{25}$ is straight or branched alkyl of 1 to 6 carbon atoms,
  or wherein R$^{23}$ and R$^{24}$ constitute a saturated hydrocarbon bridge of 3 to 5 carbon atoms which together with the nitrogen atom between them form a heterocyclic ring, or (vii) a quaternary group of the formula:

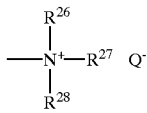

wherein R$^{26}$, R$^{27}$ and R$^{28}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

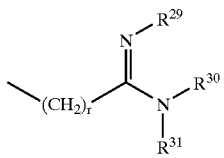

wherein r is 2, 3, 4, 5 or 6, and
R$^{29}$, R$^{30}$ and R$^{31}$ are each, independently, a hydrogen atom or alkyl of 1 to 3 carbon atoms, and wherein two of R$^{29}$, R$^{30}$ and R$^{31}$ may additionally constitute a saturated hydrocarbon bridge of 3 to 5 carbon atoms which together with the nitrogen atom(s) between them form a heterocyclic ring, (G) an guanidino group of the formula:

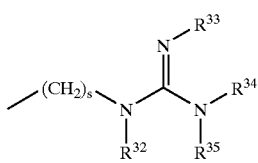

wherein s is 2, 3, 4, 5 or 6, and
R$^{32}$, R$^{33}$, R$^{34}$ and R$^{35}$ are each, independently, a hydrogen atom or alkyl of 1 to 3 carbon atoms, and wherein two of R$^{32}$, R$^{33}$, R$^{34}$ and R$^{35}$ may additionally constitute a saturated hydrocarbon bridge of 3 to 5 carbon atoms which together with the nitrogen atom(s) between them form a heterocyclic ring, (H) phenyl,
wherein one or more hydrogen atoms of said phenyl group may be optionally and independently replaced with:
  (i) alkyl of 1 to 3 carbon atoms,
  (ii) —COOH,
  (iii) —SO$_2$OH,
  (iv) —PO(OH)$_2$,
  (v) a group of the formula —COOR$^{36}$, wherein R$^{36}$ is straight or branched alkyl of 1 to 5 carbon atoms or cycloalkyl of 3 to 5 carbon atoms,
  (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring,
  (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring,
  (viii) a group of the formula —OR$^{41}$, wherein R$^{41}$ is a hydrogen atom, or an alkyl or acyl group of 1 to 7 carbon atoms,
  (ix) a group of the formula —SR$^{42}$, wherein R$^{42}$ is a hydrogen atom, or an alkyl or acyl group of 1 to 7 carbon atoms,
  (x) cyano, or
  (xi) an amidino group of the formula:

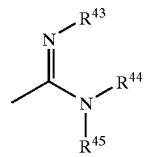

wherein R$^{43}$, R$^{44}$ and R$^{45}$ are each, independently, a hydrogen atom or alkyl of 1 to 3 carbon atoms, and wherein two of R$^{43}$, R$^{44}$ and R$^{45}$ may additionally constitute a saturated hydrocarbon bridge of 3 to 5 carbon atoms which together with the nitrogen atom(s) between them form a heterocyclic ring, (I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ constitute a saturated hydrocarbon bridge of 3 to 5 carbon atoms which together with the nitrogen atom between them form a heterocyclic ring, (J) a morpholinyl moiety, or,
(K) halogen;
X is an oxygen atom;

$R^3$ is:
(A) branched or unbranched alkyl of 1 to 3 carbon atoms or cycloalkyl of 3 to 5 carbon atoms;
$R^4$ is a group of the formula —$CH_2R^{55}$, wherein;
$R^{55}$ is:
phenyl, wherein one or more of the hydrogen atoms at the 3 and 4 positions of said phenyl group may be optionally and independently replaced with:
(A) $R^{59}$, which is aryl selected from the class consisting of phenyl, 2-, 3- or 4-pyridyl, or 2-, 4- or 5-pyrimidinyl, wherein one or more of the hydrogen atoms of said aryl group may be optionally and independently replaced with:
(i) branched or unbranched alkyl of 1 to 6 carbon atoms or cycloalkyl of 3 to 6 carbon atoms, which alkyl or cycloakyl group may be mono- or polysubstituted with halogen or oxo,
(ii) cyano,
(iii) nitro, or
(iv) halogen,
(B) methyl,
(C) branched or unbranched alkyl of 2 to 6 carbon atoms or cycloalkyl of 3 to 6 carbon atoms, which alkyl or cycloakyl group may be mono- or polysubstituted with halogen or oxo,
(D) a group of the formula —$COOR^{67}$, wherein $R^{67}$ is straight or branched alkyl of 1 to 5 carbon atoms or cycloalkyl of 3 to 5 carbon atoms,
(E) a group of the formula —$COR^{72}$, wherein $R^{72}$ is a hydrogen atom, straight or branched alkyl of 1 to 5 carbon atoms, cycloalkyl of 3 to 5 carbon atoms or $R^{59}$,
(F) a group of the formula —$OR^{73}$, wherein $R^{73}$ is a hydrogen atom, an alkyl, fluoroalkyl or acyl group of 1 to 7 carbon atoms, or $R^{59}$,
(G) a group of the formula —$SR^{74}$, wherein $R^{74}$ is a hydrogen atom, an alkyl, fluoroalkyl or acyl group of 1 to 7 carbon atoms, or $R^{59}$,
(H) cyano,
(I) nitro, or
(J) halogen;
$R^5$ is Cl;
Z is =CH—; and,
$R^7$ is Cl;
and pharmaceutically acceptable salts thereof.
Further preferred compounds of the invention are those of the formula I,
wherein:
$A^1$, $A^2$ and $A^3$ are each =CH—;
D is =$CCOR^1$— or =$CSO_2R^1$—,
$R^1$ is:
(A) a hydrogen atom,
(B) branched or unbranched alkyl of 1 to 6 carbon atoms or cycloalkyl of 3 to 6 carbon atoms, which alkyl or cycloakyl group may be mono- or polysubstituted with:
(i) oxo,
(ii) a group of the formula —$COOR^{18}$, wherein $R^{18}$ is straight or branched alkyl of 1 to 7 carbon atoms or cycloalkyl of 3 to 6 carbon atoms,
(iii) a group of the formula —$CONR^{19}R^{20}$, wherein $R^{19}$ and $R^{20}$ are each, independently, a hydrogen atom, alkyl of 1 to 6 carbon atoms or cycloalkyl of 3 to 6 carbon atoms, or wherein $R^{19}$ and $R^{20}$ constitute a saturated hydrocarbon bridge of 3 to 5 carbon atoms which together with the nitrogen atom between them form a heterocyclic ring, (iv) a group of the formula —$OR^{21}$, wherein $R^{21}$ is a hydrogen atom, or an alkyl or acyl group of 1 to 7 carbon atoms,
(v) a group of the formula —$NR^{23}R^{24}$, wherein $R^{23}$ and $R^{24}$ are each, independently,
(a) a hydrogen atom,
(b) alkyl or acyl of 1 to 7 carbon atoms or cycloalkyl of 3 to 7 carbon atoms,
(c) a group of the formula —$(CH_2)_mCOOH$, wherein m is 0, 1 or 2, or
(d) a group of the formula —$(CH_2)_nCOOR^{25}$, wherein n is 0, 1 or 2, wherein $R^{25}$ is straight or branched alkyl of 1 to 6 carbon atoms,
or wherein $R^{23}$ and $R^{24}$ constitute a saturated hydrocarbon bridge of 3 to 5 carbon atoms which together with the nitrogen atom between them form a heterocyclic ring, or
(vi) a quaternary group of the formula:

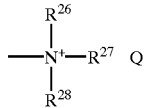

wherein $R^{26}$, $R^{27}$ and $R^{28}$ are each, independently, a branched or unbranched alkyl group of 1 to 7 carbon atoms and $Q^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula:

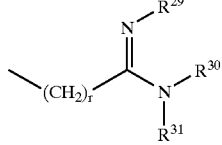

wherein r is 2, 3, 4, 5 or 6, and
$R^{29}$, $R^{30}$ and $R^{31}$ are each, independently, a hydrogen atom or alkyl of 1 to 3 carbon atoms, and wherein two of $R^{29}$, $R^{30}$ and $R^{31}$ may additionally constitute a saturated hydrocarbon bridge of 3 to 5 carbon atoms which together with the nitrogen atom(s) between them form a heterocyclic ring,
(G) an guanidino group of the formula:

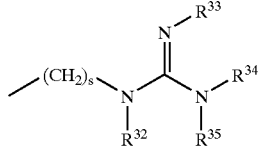

wherein s is 2, 3, 4, 5 or 6, and
$R^{32}$, $R^{33}$, $R^{34}$ and $R^{35}$ are each, independently, a hydrogen atom or alkyl of 1 to 3 carbon atoms, and wherein two of $R^{32}$, $R^{33}$, $R^{34}$ and $R^{35}$ may additionally constitute a saturated hydrocarbon bridge of 3 to 5 carbon atoms which together with the nitrogen atom(s) between them form a heterocyclic ring,

23

(H) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ constitute a saturated hydrocarbon bridge of 3 to 5 carbon atoms which together with the nitrogen atom between them form a heterocyclic ring, (I) a morpholinyl moiety, or, (J) halogen;

X is an oxygen atom;

R$^3$ is:

(A) branched or unbranched alkyl of 1 to 3 carbon atoms or cycloalkyl of 3 to 5 carbon atoms;

R$^4$ is a group of the formula —CH$_2$R$^{55}$, wherein;

R$^{55}$ is:

phenyl, wherein one or more of the hydrogen atoms at the 3 and 4 positions of said phenyl group may be optionally and independently replaced with:

(A) R$^{59}$, which is aryl selected from the class consisting of phenyl, 2-, 3- or 4-pyridyl, or 2-, 4- or 5-pyrimidinyl, wherein one or more of the hydrogen atoms of said aryl group may be optionally and independently replaced with:

(i) branched or unbranched alkyl of 1 to 6 carbon atoms or cycloalkyl of 3 to 6 carbon atoms, which alkyl or cycloakyl group may be mono- or polysubstituted with halogen or oxo, (ii) cyano, (iii) nitro, or (iv) halogen, (B) methyl, (C) branched or unbranched alkyl of 2 to 6 carbon atoms or cycloalkyl of 3 to 6 carbon atoms, which alkyl or cycloakyl group may be mono- or polysubstituted with halogen or oxo, (D) a group of the formula —COOR$^{67}$, wherein R$^{67}$ is straight or branched alkyl of 1 to 5 carbon atoms or cycloalkyl of 3 to 5 carbon atoms, (E) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$, (F) a group of the formula —OR$^{73}$, wherein R$^{73}$ is a hydrogen atom, an alkyl , fluoroalkyl or acyl group of 1 to 7 carbon atoms, or R$^{59}$, (G) a group of the formula —SR$^{74}$, wherein R$^{74}$ is a hydrogen atom, an alkyl, fluoroalkyl or acyl group of 1 to 7 carbon atoms, or R$^{59}$, (H) cyano, (I) nitro, or (J) halogen;

R$^5$ is Cl;

Z is =CH—; and,

R$^7$ is Cl;

and pharmaceutically acceptable salts thereof

Especially preferred compounds of the invention are those of the formula I wherein:

A$^1$, A$^2$ and A$^3$ are each =CH—;

D is =CCOR$^1$— or =CSO$_2$R$^1$—,

R$^1$ is (A) a hydrogen atom, (B) branched or unbranched alkyl of 1 to 6 carbon atoms or cycloalkyl of 3 to 6 carbon atoms, which alkyl or cycloakyl group may be mono- or polysubstituted with a group of the formula —OR$^{21}$, wherein

24

R$^{21}$ is a hydrogen atom, or an alkyl or acyl group of 1 to 7 carbon atoms, (C) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ constitute a saturated hydrocarbon bridge of 3 to 5 carbon atoms which together with the nitrogen atom between them form a heterocyclic ring, or (D) a morpholinyl moiety;

X is an oxygen atom;

R$^3$ is methyl;

R$^4$ is a group of the formula —CH$_2$R$^{55}$, wherein;

R$^{55}$ is:

phenyl, wherein one or more of the hydrogen atoms at the 4 position of said phenyl group may be optionally and independently replaced with:

(A) R$^{59}$, which is aryl selected from the class consisting of phenyl, 3-pyridyl, or 5-pyrimidinyl, wherein one or more of the hydrogen atoms of said aryl group may be optionally and independently replaced with:

(i) methyl, (ii) cyano, (iii) nitro, or (iv) halogen, (B) methyl, (C) cyano, (D) nitro, or (E) halogen;

R$^5$ is Cl;

Z is =CH—; and,

R$^7$ is Cl;

and pharmaceutically acceptable salts thereof.

The following are representative compounds of the invention:

3-(4-bromobenzyl)-1-(3,5-dichlorophenyl)-1,3-dihydroindol-2-one 3-(4-bromobenzyl)-1-(3,5-dichlorophenyl)-3-methyl-1,3-dihydro-indol-2-one 3-benzyl-1-(3,5-dichlorophenyl)-3-methyl-1,3-dihydroindol-2-one 3-(4-bromobenzyl)-1-(3,5-dichlorophenyl)-4-hydroxy-3-methyl-1,3-dihydroindol-2-one 3-(4-bromobenzyl)-1-(3,5-dichlorophenyl)-5-fluoro-1,3-dihydroindol-2-one 3-(4-bromobenzyl)-1-(3,5-dichlorophenyl)-1,3-dihydroindol-2-one-6-carboxylic acid 3-benzyl-1-(3,5-dichlorophenyl)-4-methoxy-1,3-dihydroindol-2-one 3-(3-bromobenzyl)-1-(3,5-dichlorophenyl)-4-methoxy-1,3-dihydroindol-2-one 3-(3-bromobenzyl)-1-(3,5-dichlorophenyl)-4-hydroxy-3-methyl-1,3-dihydroindol-2-one 3-benzyl-1-(3,5-dichlorophenyl)-4-hydroxy-1,3-dihydroindol-2-one 3-benzyl-1-(3,5-dichlorophenyl)-5-methoxy-1,3-dihydroindol-2-one 3-benzyl-1-(3,5-dichlorophenyl)-5-hydroxy-1,3-dihydroindol-2-one 3-benzyl-1-(3,5-dichlorophenyl)-1,3-dihydroindol-2-one 3-benzyl-1-(3,5-dichlorophenyl)-4-hydroxy-3-methyl-1,3-dihydroindol-2-one 3-(4-bromobenzyl)-1-(3,5-dichlorophenyl)-4-hydroxy-1,3-dihydroindol-2-one 3-(4-bromobenzyl)-1-(3,5-dichlorophenyl)-3-methyl-1,3-dihydropyrrolo[2,3-b]pyridin-2-one 3-(4-cyanobenzyl)-1-(3,5-dichlorophenyl)-3-methyl-1,3-dihydropyrrolo[2,3-b]pyridin-2-one It will be appreciated that the compounds of the formula I have at least one chiral center. Ultimately preferred are those compounds of formula I with the absolute stereochemistry depicted below in formula Ia:

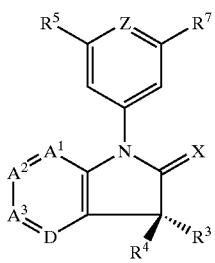

(Ia)

SYNTHESIS OF THE COMPOUNDS OF THE INVENTION

Compounds of the invention may be prepared by the general method described below. Typically, reaction progress may be monitored by thin layer chromatography (TLC) if desired. If desired, intermediates and products may be purified by chromatography on silica gel and/or recrystallization. Starting materials and reagents are either commercially available or may be prepared by one skilled in the art using methods described in the chemical literature.

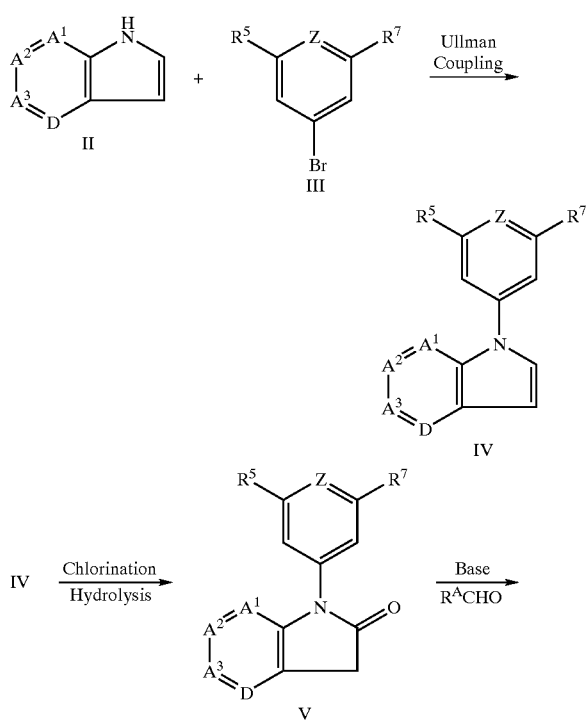

Scheme I

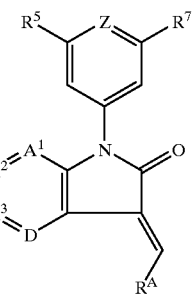

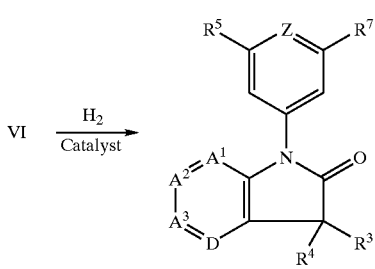

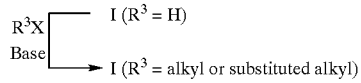

As illustrated in Scheme I, intermediate II undergoes Ullman coupling with aryl bromide III in the presence of copper and a base such as potassium carbonate in a suitable solvent such as 1,2-dichlorobenzene, preferably at the reflux temperature of the solvent. A catalytic amount of copper iodide may optionally be added. The product IV is reacted with a suitable chlorinating agent such as N-chlorosuccinimide in a suitable solvent such as acetic acid at a temperature from about room temperature to the reflux temperature of the solvent, preferably the reflux temperature. The intermediate chloro compound is then hydrolyzed, for example by diluting the cooled reaction mixture with an aqueous acid such as 70% aqueous phosphoric acid, and heating, preferably at reflux temperature, to provide V.

Intermediate V is condensed with aldehyde $R^A$CHO (the appropriate $R^4$ precursor) in a suitable solvent such as MeOH, in the presence of a base catalyst such as piperidine, preferably at the reflux temperature of the solvent to provide olefin VI. The olefin is reduced in a suitable solvent such as MeOH-acetic acid under preferably about 30 to 60 psi of hydrogen gas, in the presence of a suitable catalyst, such as 5% palladium sulfide on carbon. An additional solvent, such as dichloromethane may be added to improve solubility of the starting material (VI). The reduction product I ($R^3$=H) may then be alkylated by treating it with a base, such as potassium (trimethylsilyl)amide in a suitable solvent, such as DMF at a temperature of about 0 to −78° C. and preferably about −20 to −40° C., followed by quenching of the resulting anion with the desired alkyl halide ($R^3$X) to provide I ($R^3$ is alkyl or substituted alkyl).

An alternate method for preparing compounds of formula I, where $A^1$=N is illustrated in Scheme II, and described generally in the chemical literature (P. C. Ting et al., *J. Med. Chem.*, 1990, 33, 2697).

Scheme II

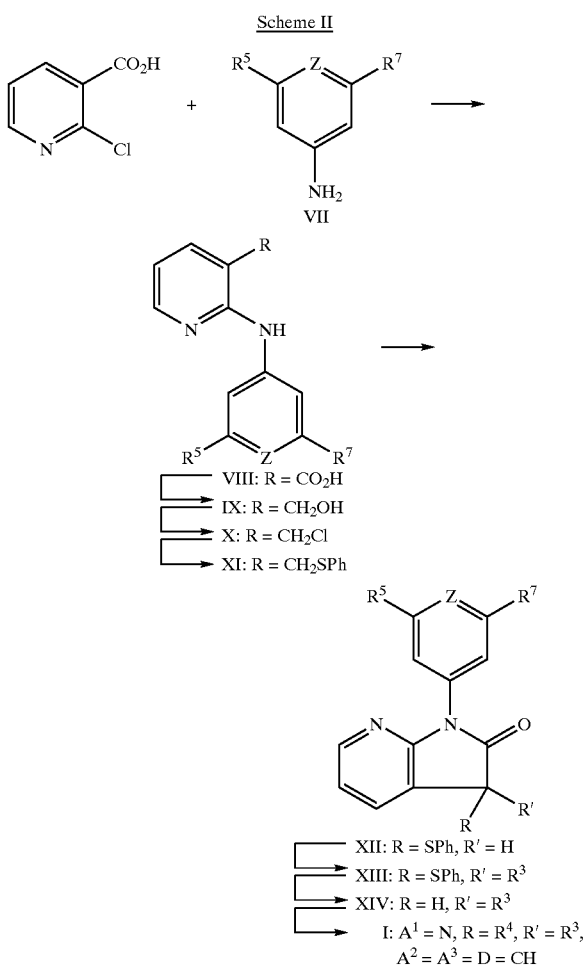

2-Chloronicotinic acid and VII are combined in a suitable solvent such as acetic acid and heated, preferably at reflux temperature for about 2–6 hr to provide VIII. This is treated with a suitable reducing agent, such as lithium aluminum hydride, in a suitable solvent, such as THF, preferably at reflux temperature, to provide IX. Treatment of IX with a suitable chlorinating agent, such as thionyl chloride provides X.

Treatment of X with thiophenol in the presence of a base, such as NaOH, in a suitable solvent, such as ethanol/water, provides thioether XI. Treatment of XI with a strong base, such as n-BuLi in a suitable solvent, such as THF, at about −30 to −78° C. followed by reaction with carbon dioxide and treatment of the resulting intermediate with an acid, such as trifluoroacetic acid, in a suitable co-solvent such as methylene chloride provides XII. Treatment of XII with a halide, preferably an iodide or bromide, $R^3X$, in the presence of a base, such as sodium hydride, in a suitable solvent such as THF at about 0° C. to ambient temperature, provides XIII. Desulfurization of XIII, for example with zinc dust and trimethylsilyl chloride in a suitable solvent, such as THF with water, provides XIV. XIV may then be treated with another halide, preferably iodide or bromide, $R^4X$, in the presence of a base, such as sodium hydride, in a suitable solvent such as THF at about 0° C. to ambient temperature, to provide I ($A^1$=N)

While the above general syntheses are illustrative of examples where X=O, the preparation of other compounds of the invention will be apparent to those skilled in the art, for example use of an agent to convert carbonyls to thiocarbonyls, such as $P_2S_3$ will provide compounds where X=S.

SYNTHETIC EXAMPLES

Example 1

Synthesis of 3-(4-Bromobenzyl)-1-(3,5-dichlorophenyl)-1,3-dihydroindol-2-one

A mixture of 5 g (43.7 mmol) of indole, 19.2 g (85.3 mmol) of 1-bromo-3,5-dichlorobenzene, 11.7 g (84.8 mmol) of potassium carbonate and 3.28 g (1.22 mmol) of copper powder in 14 mL of 1,2-dichlorobenzene was warmed at reflux. After 24 h, the mixture was cooled and diluted with dichloromethane and filtered through diatomaceous earth. The filter cake was washed with a 1:9 mixture of methanol-dichloromethane. The filtrate was pre-adsorbed onto silica gel and chromatographed on silica gel eluting with hexane. The partially purified material was placed under high vacuum to remove excess 1,2-dichlorobenzene and sublime excess 1-bromo-3,5-dichlorobenzene. A second chromatography on silica gel eluting with hexanes afforded 7.8 g (70%) of 1-(3,5-Dichlorophenyl)-1H-indole.

To a solution of 7.8 g (29.9 mmol) of 1-(3,5-Dichlorophenyl)-1H-indole in 50 mL of acetic acid was added 4.0 g (30.1 mmol) of N-chlorosuccinimide. The mixture was warmed at reflux for 1hr, when TLC indicated the disappearance of starting material. The mixture was cooled and diluted with 16 mL of 70% aqueous phosphoric acid and 4 mL of water and warmed at reflux for 6 hr. The reaction was then cooled to afford a precipitate which was diluted with 50 mL of water and collected by filtration. The solid was partially dried by pulling vacuum through the filter cake and then dissolved in dichloromethane, dried ($MgSO_4$), treated with carbon (Norit A), filtered through diatomaceous earth and concentrated to afford an orange solid. Trituration with ether gave 5.9 g (71%) of 1-(3,5-dichlorophenyl)-1,3-dihydro-indol-2-one which was used without further purification.

A mixture of 1.5 g (5.41 mmol) of the above indol-2-one, 1.5 g (8.1 mmol) of 4-bromobenzaldehyde and 0.25 mL (2.4 mmol) of piperidine in 50 mL of methanol was warmed at reflux for 4 hr. The resulting solid was cooled, collected by filtration washed with ether, and dried by pulling vacuum through the filter cake to afford 2.2 g (91%) of 3-(4-bromobenzylidene)-1-(3,5-dichlorophenyl)-1,3-dihydroindol-2-one as a yellow solid which was used without further purification.

To a suspension of 2.2 g (4.93 mmol) of the above olefin in 25 mL of methanol, 25 mL of acetic acid and 10 mL of dichloromethane was added 550 mg of 5% platinum sulfide on carbon. The reaction was placed under 45 psi of hydrogen. After 18 hr, thin-layer chromatography (2:8, EtOAc-Hexane) indicated a new polar product and starting material, so an additional 255 mg of 5% platinum sulfide on carbon was added. After an additional 4 hr under 45 psi of hydrogen the reaction was filtered through diatomaceous earth washing the catalyst with dichloromethane. The filtrate was made basic with solid/saturated aqueous sodium bicarbonate and extracted with three 30-mL portions of dichloromethane. The combined organic layers were washed with two 20 mL portions of brine, dried ($MgSO_4$), filtered and concentrated in vacuo to afford 2.1 g (95%) of crude product. Purification on silica gel using ethyl acetate-hexane (first 2.5:97.5, then 3:97, then 4:96) gave 1.78 (80%) of 3-(4-bromobenzyl)-1-(3,5-dichlorophenyl)-1,3-dihydroindol-2-one, mp 139–142° C.

Example 2

Synthesis of 3-(4-Bromobenzyl)-1-(3,5-dichlorophenyl)-3-methyl-1,3-dihydro-indol-2-one To a solution of 338 mg (0.75 mmol) of the product of Example 1 in 15 mL of anhydrous dimethylformamide cooled to 40° C. was added 1.75 mL (0.87 mmol) of a 0.5 M solution of potassium bis(trimethylsilyl)amide in toluene. After 15 min, 0.5 mL (8.08 mmol) of iodomethane was added. The mixture stirred for 5 min at −20° C. and was then quenched with 200 mL of saturated aqueous ammonium chloride and extracted with three 30 mL portions of ethyl acetate. The combined organic layers were washed with three 20 mL portions of brine, dried (MgSO$_4$), filtered and concentrated in vacuo. The residue was adsorbed onto silica gel and chromatographed over silica gel using hexane to pack the column and ethyl acetate-hexane to elute the product (first 2:98, then 5:95) to afford a white solid which was recrystallized from ether-hexane to afford 159 mg (45%) of the title compound: mp 129–130° C.

Example 3

Synthesis of 3-(4-Bromobenzyl)-1-(3,5-dichlorophenyl)-3-methyl-1,3-dihydropyrrolo[2,3-b]pyridin-2-one 2-Chloronicotinic acid (10 g) was combined with 3,5-dichloroaniline (15 g) in 150 mL acetic acid and heated at reflux for 4 hr. Upon cooling, a white solid formed which was collected by filtration, washed with acetic acid, water, and dried to give 17.6 g of 2-(3,5-dichlorophenylamino)nicotinic acid.

A solution of the above acid in 100 mL THF was added to 2.1 g LiAlH4 in 200 mL THF over 30 min while cooling on ice. After stirring at room temperature for 1 hr, the reaction was refluxed for 1 hr. The reaction was then cooled, 20 mL EtOAc was added and the mixture concentrated on a rotary evaporator. The residue was combined with 500 mL EtOAc and extracted with water. The organic phase was dried and concentrated to give 6.2 g of [2-(3,5-dichlorophenylamino)pyridin-3-yl]methanol.

Thionyl chloride (15 mL) was added slowly to a solution of 6.0 g of the above alcohol in 100 mL methylene chloride and the reaction stirred at room temperature for 18 hr. The reaction was concenterated, the residue dissolved in 150 mL methylene chloride and washed with 10% NaHCO$_3$ solution. The organic layer was dried (Na$_2$SO$_4$) and concentrated to give 6.3 g of (3-chloromethylpyridin-2-yl) (3,5-dichlorophenyl)amine.

A solution of 6 g of the above amine in 50 mL EtOH was combined with a solution of 1.83 g NaOH and 2.53 g of thiophenol in 50 mL water. The reaction was stirred at room temperature for 18 hr. Water (100 mL) was added and the resulting precipitate collected, rinsed with water and dried to give 5.5 g of (3,5-dichlorophenyl) [(3-phenylthiomethyl)pyridin-2-yl]amine.

A solution of 5.5 g of the above thioether in 100 mL dry THF was cooled to −78° C. under nitrogen. A 2.5 M solution of n-BuLi in hexane (30.4 mL) was added dropwise over 5 min. After stirring for 3 hr at −78° C. and 15 min at −30° C., the reaction was re-cooled to −78° C., poured over a stirred suspension of 500 g dry ice in 500 mL dry ether and stirred for 3 hr at ambient temperature. The reaction was then concentrated, and the residue dissolved in 500 mL water, and extracted with 300 mL ether. The aqueous layer was adjusted to pH 3 and extracted with methylene chloride. The organic layers were combined, dried (Na$_2$SO$_4$), and concentrated. The gummy residue was dissolved in 25 mL methylene chloride and 10 mL trifluoroacetic acid and stirred overnight at ambient temperature. The reaction mixture was then concentrated, dissolved in 200 mL methylene chloride, washed three times with saturated NaHCO$_3$ solution, dried (Na$_2$SO$_4$) and concentrated. The resulting solid was washed with hexane and dried to give the desired 1-(3,5-dichlorophenyl)-3-phenylthio-1,3-dihydropyrrolo[2,3-b]pyridin-2-one.

450 mg of a 60% NaH in mineral oil dispersion was washed with hexane and suspended in 25 mL THF, under nitrogen. A solution of 2 g of the above intermediate in 10 mL THF was added dropwise at 0° C. After stirring 1 hr, 3 mL iodomethane was added. The reaction was stirred at room temperature overnight, concentrated, the residue dissolved in 100 mL ether, washed with 10% NaHCO$_3$ solution, dried (Na$_2$SO$_4$), and concentrated to give 1-(3,5-dichlorophenyl)-3-methyl-3-phenylthio-1,3-dihydropyrrolo[2,3-b]pyridin-2-one.

900 mg of the above intermediate was added to a suspension of 797 mg Zn dust in 16.3 mL THF plus 1.63 mL H$_2$0. The reaction was stirred in a water bath at ambient temperature and 1.86 g of trimethylsilyl chloride was added via syringe over 30 min. After stirring overnight at room temperature, the reaction was diluted with 50 mL THF, filtered, and poured into a rapidly stirred mixture of 100 mL EtOAc and 100 mL 1N NaOH. The aqueous phase was extracted with an additional 100 mL EtOAc, the combined organic layers dried (Na$_2$SO$_4$) and concentrated. The resulting oil was triturated with hexane giving the desired 1-(3,5-dichlorophenyl)-3-methyl-1,3-dihydropyrrolo[2,3-b]pyridin-2-one.

388 mg of a 60% NaH in mineral oil dispersion was washed with hexane and suspended in 15 mL THF, under nitrogen. The suspension was cooled to 0° C. and 500 mg of the above intermediate in 20 mL THF was added dropwise. The reaction was removed from the ice-bath, stirred for 30 min, and re-cooled to 0° C. 4-Bromobenzyl bromide (969 mg) was added and the reaction stirred at room temperature for 16 hr. The reaction was concentrated and extracted with EtOAc (2×100 mL) from 100 mL saturated NaHCO$_3$ solution. The combined organic layers were washed with brine, dried (Na$_2$SO$_4$) and concentrated. The residue was flash chromatographed on silica gel, eluting with 90 hexane/10 EtOAc to give 606 mg of the title compound, m.p. 91–92° C.

Table 1 illustrates additional compounds of the invention which were prepared by methods analogous to those described above.

TABLE 1

Compounds of Formula (I).

$$\begin{array}{c} R^5 \diagdown Z \diagup R^7 \\ \text{(aryl—N—pyrrolinone structure)} \end{array}$$

| Cpd | A¹ | A² | A³ | D | X | R³ | R⁴ | R⁵ | R⁷ | Z | m.p. °C. |
|---|---|---|---|---|---|---|---|---|---|---|---|
| 4 | C[a] | C | C | C | O | Me | —CH₂Ph | Cl | Cl | C | |
| 5 | N | C | C | C | O | Me | —CH₂Ph4CN | Cl | Cl | C | |
| 6 | C | C | C | C—OH | O | Me | —CH₂Ph4Br | Cl | Cl | C | 225–227 |
| 7 | C | C | C—F | C | O | H | —CH₂Ph4Br | Cl | Cl | C | 178–179 |
| 8 | C | C—CO₂H | C | C | O | H | —CH₂Ph4Br | Cl | Cl | C | 264–266 |
| 9 | C | C | C | C—OMe | O | H | —CH₂Ph | Cl | Cl | C | 138–140 |
| 10 | C | C | C | C—OMe | O | H | —CH₂Ph3Br | Cl | Cl | C | 142–144 |
| 11 | C | C | C | C—OH | O | Me | —CH₂Ph3Br | Cl | Cl | C | 225–227 |
| 12 | C | C | C | C—OH | O | H | —CH₂Ph | Cl | Cl | C | 181–185 |
| 13 | C | C | C—OMe | C | O | H | —CH₂Ph | Cl | Cl | C | 118–119 |
| 14 | C | C | C—OH | C | O | H | —CH₂Ph | Cl | Cl | C | 232–235 |
| 15 | C | C | C | C | O | H | —CH₂Ph | Cl | Cl | C | 109–111 |
| 16 | C | C | C | C—OH | O | Me | —CH₂Ph | Cl | Cl | C | 165–166.5 |
| 17 | C | C | C | C—OH | O | H | —CH₂Ph4Br | Cl | Cl | C | 203–208 |

[a]C indicates a carbon substituted with hydrogen (CH).

Description of Biological Properties

The biological properties of representative compounds of the formula I were investigated by way of the experimental protocol described below. The results of such testing are reported in Table 2, which appears below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654–2660). The LFA-1 is purified from SKW3 lysates by immunoaffinity chromatography on TS2/4 LFA-1 mAb Sepharose and eluted at pH 11.5 in the presence of 2 mM MgCl₂ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature*, 1990, 344, 70–72 and see Arruda, A.; et al., *Antimicrob. Agents Chemother.* 1992, 36, 1186–1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 μg/mL in Dulbecco's phosphate buffered saline with calcium and magnesium, additional 2 mM MgCl₂ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 µg/mL) is used as a positive control for inhibition of the LFA-1/ICAM-1 interaction. The lack of the addition of LFA-1 to the binding assay is used as a background control for all samples. A dose-response curve is obtained for all test compounds.

Results of tests are reported in Table 2 as $K_d$'s in µM.

TABLE 2

Inhibition of LFA-1 Binding to ICAM-1

| Example No. | Kd (µM) |
|---|---|
| 1 | >10 |
| 2 | >10 |
| 3 | 0.375 |
| 4 | 0.808 |
| 5 | 3.53 |
| 6 | 1.79 |
| 7 | 2.71 |
| 8 | 4.89 |
| 9 | 0.705 |
| 10 | 1.08 |
| 11 | 2.54 |
| 12 | 1.31 |
| 13 | >10 |
| 14 | >10 |
| 15 | 4.97 |
| 16 | 1.44 |
| 17 | 0.917 |

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a "prophylactic" or "therapeutic" purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

Formulations

Compounds of the formula I can be formulated for therapeutic administration in a number of ways. Descriptions of several exemplary formulations are given below.

Example A

Capsules or Tablets

| Example A-1 | | Example A-2 | |
| --- | --- | --- | --- |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
| --- | --- |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

Suspension

| Ingredients | Quantity |
| --- | --- |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

What is claimed is:

1. A compound of the formula I:

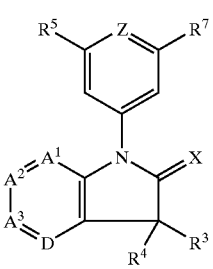

wherein:

$A^1$, $A^2$ and $A^3$ are each, independently, =N— or =CH—;
D is =N—, =CR$^1$—, =CSO$_2$R$^1$—, =CSOR$^1$—, =CSR$^1$—, =COR$^1$—, =CCOR$^1$—, or =CNHR$^1$—,
  wherein R$^1$ is:
  (A) a hydrogen atom,
  (B) branched or unbranched alkyl of 1 to 6 carbon atoms or cycloalkyl of 3 to 6 carbon atoms, which alkyl or cycloakyl group is optionally mono- or polysubstituted with:
    (i) halogen,
    (ii) oxo,
    (iii) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
    wherein one or more hydrogen atoms of said aryl group is optionally and independently replaced with:
      (a) alkyl of 1 to 3 carbon atoms,
      (b) —COOH,
      (c) —SO$_2$OH,
      (d) —PO(OH)$_2$, (e) a group of the formula —COOR$^8$, wherein R$^8$ is straight or branched alkyl of 1 to 5 carbon atoms or cycloalkyl of 3 to 5 carbon atoms, (f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ form a saturated hydrocarbon bridge of 3 to 5 carbon atoms which together with the nitrogen atom between them form a heterocyclic ring, (g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ form a saturated hydrocarbon bridge of 3 to 5 carbon atoms which together with the nitrogen atom between them form a heterocyclic ring, (h) a group of the formula —OR$^{13}$, wherein R$^{13}$ is a hydrogen atom, or an alkyl or acyl group of 1 to 7 carbon atoms, (i) a group of the formula —SR$^{14}$, wherein R$^{14}$ is a hydrogen atom, or an alkyl or acyl group of 1 to 7 carbon atoms, (j) cyano, or (k) an amidino group of the formula:

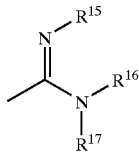

wherein R$^{15}$, R$^{16}$ and R$^{17}$ are each, independently, a hydrogen atom or alkyl of 1 to 3 carbon atoms, or wherein one of R$^{15}$, R$^{16}$ and R$^{17}$ is a hydrogen atom or alkyl of 1 to 3 carbon atoms and wherein the remaining two of R$^{15}$, R$^{16}$ and R$^{17}$ together form a saturated hydrocarbon bridge of 3 to 5 carbon atoms which together with the nitrogen atom(s) between them form a heterocyclic ring, (iv) a group of the formula —COOR$^{18}$, wherein R$^{18}$ is straight or branched alkyl of 1 to 7 carbon atoms or cycloalkyl of 3 to 6 carbon atoms, (v) cyano, (vi) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ together form a saturated hydrocarbon bridge of 3 to 5 carbon atoms which together with the nitrogen atom between them form a heterocyclic ring, (vii) a group of the formula —OR$^{21}$, wherein R$^{21}$ is a hydrogen atom, or an alkyl or acyl group of 1 to 7 carbon atoms, (viii) a group of the formula —SR$^{22}$, wherein R$^{22}$ is a hydrogen atom, or an alkyl or acyl group of 1 to 7 carbon atoms, (ix) a group of the formula —NR$^{23}$R$^{24}$, wherein R$^{23}$ and R$^{24}$ are each, independently, (a) a hydrogen atom, (b) alkyl or acyl of 1 to 7 carbon atoms or cycloalkyl of 3 to 7 carbon atoms, (c) a group of the formula —(CH$_2$)$_m$COOH, wherein m is 0, 1 or 2, or (d) a group of the formula —(CH$_2$)$_n$COOR$^{25}$, wherein n is 0, 1 or 2, wherein R$^{25}$ is straight or branched alkyl of 1 to 6 carbon atoms, or wherein R$^{23}$ and R$^{24}$ together form a saturated hydrocarbon bridge of 3 to 5 carbon atoms which together with the nitrogen atom between them form a heterocyclic ring, or (x) a quaternary group of the formula:

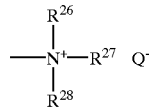

wherein R$^{26}$, R$^{27}$ and R$^{28}$ are each, independently, a branched or unbranched alkyl group of 1 to 7 carbon atoms and Q$^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

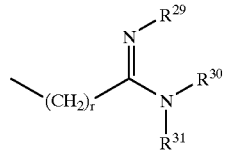

wherein r is 2, 3, 4, 5 or 6, and

R$^{29}$, R$^{30}$ and R$^{31}$ are each, independently, a hydrogen atom or alkyl of 1 to 3 carbon atoms, or wherein one of R$^{29}$, R$^{30}$ and R$^{31}$ is a hydrogen atom or alkyl of 1 to 3 carbon atoms and wherein the remaining two of R$^{29}$, R$^{30}$ and R$^{31}$ together form a saturated hydrocarbon bridge of 3 to 5 carbon atoms which together with the nitrogen atom(s) between them form a heterocyclic ring, (G) an guanidino group of the formula:

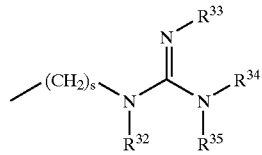

wherein s is 2, 3, 4, 5 or 6, and

R$^{32}$, R$^{33}$, R$^{34}$ and R$^{35}$ are each, independently, a hydrogen atom or alkyl of 1 to 3 carbon atoms, or wherein one of R$^{32}$, R$^{33}$, R$^{34}$ and is a hydrogen atom or alkyl of 1 to 3 carbon atoms wherein the remaining two of R$^{32}$, R$^{33}$, R$^{34}$ and R$^{35}$ together form a saturated hydrocarbon bridge of 3 to 5 carbon atoms which together with the nitrogen atom(s) between them form a heterocyclic ring, (H) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
wherein one or more hydrogen atoms of said aryl group is optionally and independently replaced with:
(i) alkyl of 1 to 3 carbon atoms,
(ii) —COOH,
(iii) —SO$_2$OH,
(iv) —PO(OH)$_2$,
(v) a group of the formula —COOR$^{36}$, wherein R$^{36}$ is straight or branched alkyl of 1 to 5 carbon atoms or cycloalkyl of 3 to 5 carbon atoms,
(vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ together form a saturated hydrocarbon bridge of 3 to 5 carbon atoms which together with the nitrogen atom between them form a heterocyclic ring,
(vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ together form a saturated hydrocarbon bridge of 3 to 5 carbon atoms which together with the nitrogen atom between them form a heterocyclic ring,
(viii) a group of the formula —CR$^{41}$, wherein R$^{41}$ is a hydrogen atom, or an alkyl or acyl group of 1 to 7 carbon atoms,
(ix) a group of the formula —SR$^{42}$, wherein R$^{42}$ is a hydrogen atom, or an alkyl or acyl group of 1 to 7 carbon atoms,
(x) cyano, or
(xi) an amidino group of the formula:

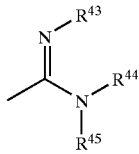

wherein R$^{43}$, R$^{44}$ and R$^{45}$ are each, independently, a hydrogen atom or alkyl of 1 to 3 carbon atoms, or wherein one of R$^{43}$, R$^{44}$ and R$^{45}$ is a hydrogen atom or alkyl of 1 to 3 carbon atoms and wherein the remaining two of R$^{43}$, R$^{44}$ and R$^{45}$ together form a saturated hydrocarbon bridge of 3 to 5 carbon atoms which together with the nitrogen atom(s) between them form a heterocyclic ring,
(I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ together form a saturated hydrocarbon bridge of 3 to 5 carbon atoms which together with the nitrogen atom between them form a heterocyclic ring,
(J) a morpholinyl moiety, or,
(K) halogen;
X is an oxygen or sulfur atom;
R$^3$ is:

(A) a hydrogen atom, or
(B) branched or unbranched alkyl of 1 to 3 carbon atoms or cycloalkyl of 3 to 5 carbon atoms wherein said alkyl or cycloalkyl group may optionally be substituted with:
(i) a group of the formula —OR$^{48}$, wherein R$^{48}$ is a hydrogen atom, or an alkyl or acyl group of 1 to 7 carbon atoms, or
(ii) a group of the formula —NR$^{49}$R$^{50}$, wherein R$^{49}$ and R$^{50}$ are each, independently, a hydrogen atom, alkyl of 1 to 2 carbon atoms, or acyl of 1 to 2 carbon atoms;
R$^4$ is a group of the formula —(CR$^{51}$R$^{52}$)$_x$(CR$^{53}$R$^{54}$)$_y$R$^{55}$, wherein;
x and y are each independently 0 or 1,
R$^{51}$, R$^{52}$ and R$^{53}$ are each, independently:
(A) a hydrogen atom,
(B) a group of the formula —OR$^{56}$, wherein R$^{56}$ is a hydrogen atom, or an alkyl or acyl group of 1 to 7 carbon atoms, or
(C) branched or unbranched alkyl of 1 to 3 carbon atoms or cycloalkyl of 3 to 5 carbon atoms,
R$^{54}$ is:
(A) a group of the formula R$^{57}$, wherein R$^{57}$ is defined similarly to R$^1$ above, or
(B) a group of the formula —OR$^{58}$, wherein R$^{58}$ is defined similarly to R$^1$ above;
R$^{55}$ is:
aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group is optionally and independently replaced with:
(A) R$^{59}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl, wherein one or more of the hydrogen atoms of said aryl group is optionally and independently replaced with:
  (i) branched or unbranched alkyl of 1 to 6 carbon atoms or cycloalkyl of 3 to 6 carbon atoms, which alkyl or cycloakyl group is optionally mono- or polysubstituted with halogen or oxo,
  (ii) a group of the formula —COOR$^{60}$, wherein R$^{60}$ is straight or branched alkyl of 1 to 5 carbon atoms or cycloalkyl of 3 to 5 carbon atoms,
  (iii) a group of the formula —NR$^{61}$R$^{62}$, wherein R$^{61}$ and R$^{62}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{61}$ and R$^{62}$ together form a saturated hydrocarbon bridge of 3 to 5 carbon atoms which together with the nitrogen atom between them form a heterocyclic ring,
  (iv) a group of the formula —CONR$^{63}$R$^{64}$, wherein R$^{63}$ and R$^{64}$ are each, independently, a hydrogen atom, alkyl or fluoroalkyl of 1 to 6 carbon atoms or cycloalkyl of 3 to 6 carbon atoms, or wherein R$^{63}$ and R$^{64}$ together form a saturated hydrocarbon bridge of 3 to 5 carbon atoms which together with the nitrogen atom between them form a heterocyclic ring,
  (v) a group of the formula —OR$^{65}$, wherein R$^{65}$ is a hydrogen atom, or an alkyl, fluoroalkyl or acyl group of 1 to 7 carbon atoms,
  (vi) a group of the formula —SR$^{66}$, wherein R$^{66}$ is a hydrogen atom, or an alkyl, fluoroalkyl or acyl group of 1 to 7 carbon atoms,
  (vii) cyano,
  (viii) nitro, or
  (ix) halogen,
(B) methyl, which is optionally mono- or polysubstituted with fluorine atoms and additionally optionally monosubstituted with R$^{59}$,
(C) branched or unbranched alkyl of 2 to 6 carbon atoms or cycloalkyl of 3 to 6 carbon atoms, which alkyl or cycloakyl group is optionally mono- or polysubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —NR$^{68}$R$^{69}$, wherein R$^{68}$ and R$^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{68}$ and R$^{69}$ together form a saturated hydrocarbon bridge of 3 to 5 carbon atoms which together with the nitrogen atom between them form a heterocyclic ring, and wherein one of R$^{68}$ and R$^{69}$ may additionally be the group R$^{59}$,
(F) a group of the formula —CONR$^{70}$R$^{71}$, wherein R$^{70}$ and R$^{71}$ are each, independently, a hydrogen atom, alkyl or fluoroalkyl of 1 to 6 carbon atoms or cycloalkyl of 3 to 6 carbon atoms, or wherein R$^{70}$ and R$^{71}$ together form a saturated hydrocarbon bridge of 3 to 5 carbon atoms which together with the nitrogen atom between them form a heterocyclic ring, and wherein one of R$^{70}$ and R$^{71}$ may additionally be the group R$^{59}$,
(G) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$,
(H) a group of the formula —OR$^{73}$, wherein R$^{73}$ is a hydrogen atom, an alkyl, fluoroalkyl or acyl group of 1 to 7 carbon atoms, or R$^{59}$,
(I) a group of the formula —SR$^{74}$, wherein R$^{74}$ is a hydrogen atom, an alkyl, fluoroalkyl or acyl group of 1 to 7 carbon atoms, or R$^{59}$,
(J) cyano,
(K) nitro, or
(L) halogen;
R$^5$ is Cl or trifluoromethyl;
Z is =N— or =CR$^6$—
  wherein R$^6$ is a hydrogen, fluorine, chlorine, bromine or iodine atom, methyl or trifluoromethyl; and,
R$^7$ is a hydrogen, fluorine, chlorine, bromine or iodine atom, methyl, cyano, nitro or trifluoromethyl, with the condition that when Z is N or =CH—, R$^7$ is chlorine or trifluoromethyl;
or a pharmaceutically acceptable salt thereof.

2. A compound of the formula I as, in accordance with claim 1, wherein:
A$^1$, A$^2$ and A$^3$ are each, independently, =N— or =CH—;
D is =N—, =CR$^1$—, =CSO$_2$R$^1$—, =CSOR$^1$—, =CSR$^1$—, =COR$^1$—, =CCOR$^1$—, or =CNHR$^1$—,
wherein R$^1$ is:
  (A) a hydrogen atom,
  (B) branched or unbranched alkyl of 1 to 6 carbon atoms or cycloalkyl of 3 to 6 carbon atoms, which alkyl or cycloakyl group is optionally mono- or polysubstituted with:
    (i) halogen,
    (ii) oxo,
    (iii) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b] furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
  wherein one or more hydrogen atoms of said aryl group is optionally and independently replaced with:
    (a) alkyl of 1 to 3 carbon atoms,
    (b) —COOH,
    (c) —SO$_2$OH,
    (d) —PO(OH)$_2$,
    (e) a group of the formula —COOR$^8$, wherein R$^8$ is straight or branched alkyl of 1 to 5 carbon atoms or cycloalkyl of 3 to 5 carbon atoms,
    (f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ together form a saturated hydrocarbon bridge of 3 to 5 carbon atoms which together with the nitrogen atom between them form a heterocyclic ring,
    (g) a group of the formula —CONR$^{11}$ R$^{12}$, wherein R$^{11}$ and R$^{12}$ are each independently a hydrogen atom, alkyl of 1 to 6 carbon atoms or cycloalkyl of 3 to 6 carbon atoms, or wherein $R^{11}$ and $R^{12}$ together form a saturated hydrocarbon bridge of 3 to 5 carbon atoms which together with the nitrogen atom between them form a heterocyclic ring, (h) a group of the formula —$OR^{13}$, wherein $R^{13}$ is a hydrogen atom, or an alkyl or acyl group of 1 to 7 carbon atoms, (i) a group of the formula —$SR^{14}$, wherein $R^{14}$ is a hydrogen atom, or an alkyl or acyl group of 1 to 7 carbon atoms, (j) cyano, or (k) an amidino group of the formula:

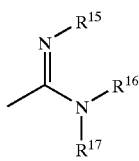

wherein $R^{15}$, $R^{16}$ and $R^{17}$ are each, independently, a hydrogen atom or alkyl of 1 to 3 carbon atoms, or wherein one of $R^{15}$, $R^{16}$ and $R^{17}$ is a hydrogen atom or alkyl of 1 to 3 carbon atoms and wherein the remaining two of $R^{15}$, $R^{16}$ and $R^{17}$ together form a saturated hydrocarbon bridge of 3 to 5 carbon atoms which together with the nitrogen atom(s) between them form a heterocyclic ring, (iv) a group of the formula —$COOR^{18}$, wherein $R^{18}$ is straight or branched alkyl of 1 to 7 carbon atoms or cycloalkyl of 3 to 6 carbon atoms, (v) cyano, (vi) a group of the formula —$CONR^{19}R^{20}$, wherein $R^{19}$ and $R^{20}$ are each, independently, a hydrogen atom, alkyl of 1 to 6 carbon atoms or cycloalkyl of 3 to 6 carbon atoms, or wherein $R^{19}$ and $R^{20}$ together form a saturated hydrocarbon bridge of 3 to 5 carbon atoms which together with the nitrogen atom between them form a heterocyclic ring, (vii) a group of the formula —$OR^{21}$, wherein $R^{21}$ is a hydrogen atom, or an alkyl or acyl group of 1 to 7 carbon atoms, (viii) a group of the formula —$SR^{22}$, wherein $R^{22}$ is a hydrogen atom, or an alkyl or acyl group of 1 to 7 carbon atoms, (ix) a group of the formula —$NR^{23}R^{24}$, wherein $R^{23}$ and $R^{24}$ are each, independently,
  (a) a hydrogen atom,
  (b) alkyl or acyl of 1 to 7 carbon atoms or cycloalkyl of 3 to 7 carbon atoms,
  (c) a group of the formula —$(CH_2)_mCOOH$, wherein m is 0, 1 or 2, or
  (d) a group of the formula —$(CH_2)_nCOOR^{25}$, wherein n is 0, 1 or 2, wherein $R^{25}$ is straight or branched alkyl of 1 to 6 carbon atoms,
  or wherein $R^{23}$ and $R^{24}$ together form a saturated hydrocarbon bridge of 3 to 5 carbon atoms which together with the nitrogen atom between them form a heterocyclic ring, or (x) a quaternary group of the formula:

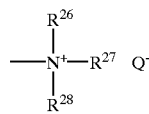

wherein $R^{26}$, $R^{27}$ and $R^{28}$ are each, independently, a branched or unbranched alkyl group of 1 to 7 carbon atoms and $Q^-$ is a chlorine, bromine or iodine counterion, (C) a branched or unbranched carboxylic acid group of 3 to 6 carbon atoms, (D) a branched or unbranched phosphonic acid group of 2 to 6 carbon atoms, (E) a branched or unbranched sulfonic acid group of 2 to 6 carbon atoms, (F) an amidino group of the formula:

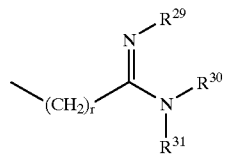

wherein r is 2, 3, 4, 5 or 6 and
one of $R^{29}$, $R^{30}$ and $R^{31}$ is a hydrogen atom or alkyl of 1 to 3 carbon atoms, and wherein the remaining two of $R^{29}$, $R^{30}$ and $R^{31}$ together form a saturated hydrocarbon bridge of 3 to 5 carbon atoms which together with the nitrogen atom(s) between them form a heterocyclic ring, (G) an guanidino group of the formula:

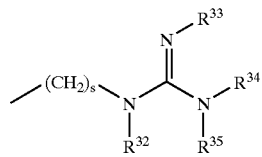

wherein s is 2, 3, 4, 5 or 6, and
$R^{32}$, $R^{33}$, $R^{34}$ and $R^{35}$ are each, independently, a hydrogen atom or alkyl of 1 to 3 carbon atoms, or wherein two of $R^{32}$, $R^{33}$, $R^{34}$ and $R^{35}$ are each, independently, a hydrogen atom or alkyl of 1 to 3 carbon atoms wherein the remaining two of $R^{32}$, $R^{33}$, $R^{34}$ and $R^{35}$ together form a saturated hydrocarbon bridge of 3 to 5 carbon atoms which together with the nitrogen atom(s) between them form a heterocyclic ring, (H) aryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl group is optionally and independently replaced with:

(i) alkyl of 1 to 3 carbon atoms,
(ii) —COOH,
(iii) —SO$_2$OH,
(iv) —PO(OH)$_2$,
(v) a group of the formula —COOR$^{36}$, wherein R$^{36}$ is straight or branched alkyl of 1 to 5 carbon atoms or cycloalkyl of 3 to 5 carbon atoms,
(vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ together form a saturated hydrocarbon bridge of 3 to 5 carbon atoms which together with the nitrogen atom between them form a heterocyclic ring,
(vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ together form a saturated hydrocarbon bridge of 3 to 5 carbon atoms which together with the nitrogen atom between them form a heterocyclic ring,
(viii) a group of the formula —OR$^{41}$, wherein R$^{41}$ is a hydrogen atom, or an alkyl or acyl group of 1 to 7 carbon atoms,
(ix) a group of the formula —SR$^{42}$, wherein R$^{42}$ is a hydrogen atom, or an alkyl or acyl group of 1 to 7 carbon atoms,
(x) cyano, or
(xi) an amidino group of the formula:

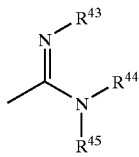

wherein R$^{43}$, R$^{44}$ and R$^{45}$ are each, independently, a hydrogen atom or alkyl of 1 to 3 carbon atoms, or wherein one of R$^{43}$, R$^{44}$ and R$^{45}$ is a hydrogen atom or alkyl of 1 to 3 carbon atoms and wherein the remaining two of R$^{43}$, R$^{44}$ and R$^{45}$ together form a saturated hydrocarbon bridge of 3 to 5 carbon atoms which together with the nitrogen atom(s) between them form a heterocyclic ring,
(I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ together form a saturated hydrocarbon bridge of 3 to 5 carbon atoms which together with the nitrogen atom between them form a heterocyclic ring,
(J) a morpholinyl moiety, or,
(K) halogen;
X is an oxygen or sulfur atom;
R$^3$ is:
(A) a hydrogen atom, or
(B) branched or unbranched alkyl of 1 to 3 carbon atoms or cycloalkyl of 3 to 5 carbon atoms wherein said alkyl or cycloalkyl group may optionally be substituted with:
(i) a group of the formula —OR$^{48}$, wherein R$^{48}$ is a hydrogen atom, or an alkyl or acyl group of 1 to 7 carbon atoms, or (ii) a group of the formula —NR$^{49}$R$^{50}$, wherein R$^{49}$ and R$^{50}$ are each, independently, a hydrogen atom, alkyl of 1 to 2 carbon atoms, or acyl of 1 to 2 carbon atoms;
R$^4$ is a group of the formula —CH$_2$R$^{55}$, wherein:
R$^{55}$ is:
aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b] furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group is optionally and independently replaced with:
(A) R$^{59}$, which is aryl selected from the class consisting of phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b] furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-pthalaninyl, 2-, 3-, 6- or 7-quinoxalinyl, 2-, 3-, 6- or 7-napthyridinyl, 2-, 6- or 7-pteridinyl and 2-, 6- or 7-quinazolinyl,
wherein one or more of the hydrogen atoms of said aryl group is optionally and independently replaced with:
(i) branched or unbranched alkyl of 1 to 6 carbon atoms or cycloalkyl of 3 to 6 carbon atoms, which alkyl or cycloakyl group is optionally mono- or polysubstituted with halogen or oxo,
(ii) cyano,
(iii) nitro, or
(iv) halogen,
(B) methyl, which is optionally mono- or polysubstituted with fluorine atoms and additionally is optionally monosubstituted with R$^{59}$,
(C) branched or unbranched alkyl of 2 to 6 carbon atoms or cycloalkyl of 3 to 6 carbon atoms, which alkyl or cycloakyl group is optionally mono- or polysubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —NR$^{68}$R$^{69}$, wherein R$^{68}$ and R$^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{68}$ and $R^{69}$ together form a saturated hydrocarbon bridge of 3 to 5 carbon atoms which together with the nitrogen atom between them form a heterocyclic ring, and wherein one of $R^{68}$ and $R^{69}$ may additionally be the group $R^{59}$, (F) a group of the formula —$CONR^{70}R^{71}$, wherein $R^{70}$ and $R^{71}$ are each, independently, a hydrogen atom, alkyl or fluoroalkyl of 1 to 6 carbon atoms or cycloalkyl of 3 to 6 carbon atoms, or wherein $R^{70}$ and $R^{71}$ together form a saturated hydrocarbon bridge of 3 to 5 carbon atoms which together with the nitrogen atom between them form a heterocyclic ring, and wherein one of $R^{70}$ and $R^{71}$ may additionally be the group $R^{59}$, (G) a group of the formula —$COR^{72}$, wherein $R^{72}$ is a hydrogen atom, straight or branched alkyl of 1 to 5 carbon atoms, cycloalkyl of 3 to 5 carbon atoms or $R^{59}$, (H) a group of the formula —$OR^{73}$, wherein $R^{73}$ is a hydrogen atom, an alkyl, fluoroalkyl or acyl group of 1 to 7 carbon atoms, or $R^{59}$, (I) a group of the formula —$SR^{74}$, wherein $R^{74}$ is a hydrogen atom, an alkyl, fluoroalkyl or acyl group of 1 to 7 carbon atoms, or $R^{59}$, (J) cyano,
(K) nitro, or
(L) halogen;

$R^5$ is Cl or trifluoromethyl;
Z is =N— or =$CR^6$—
  wherein $R^6$ is a hydrogen, fluorine, chlorine, bromine or iodine atom, methyl or trifluoromethyl; and,
$R^7$ is a hydrogen, fluorine, chlorine, bromine or iodine atom, methyl, cyano, nitro or trifluoromethyl, with the condition that when Z is N or =CH—, $R^7$ is chlorine or trufluoromethyl;
or a pharmaceutically acceptable salt thereof.

3. A compound of the formula I, in accordance with claim 1, wherein:
$A^1$, $A^2$ and $A^3$ are each, independently, =N— or =CH—;
D is =N—, =$CR^1$—, =$COR^1$—, =$CCOR^1$—, or =$CSO_2R^1$—,
wherein $R^1$ is:
  (A) a hydrogen atom,
  (B) branched or unbranched alkyl of 1 to 6 carbon atoms or cycloalkyl of 3 to 6 carbon atoms, which alkyl or cycloakyl group is optionally mono- or polysubstituted with:
    (i) oxo,
    (ii) phenyl,
    wherein one or more hydrogen atoms of said phenyl group is optionally and independently replaced with:
      (a) alkyl of 1 to 3 carbon atoms,
      (b) —COOH,
      (c) —$SO_2OH$,
      (d) —$PO(OH)_2$,
      (e) a group of the formula —$COOR^8$, wherein $R^8$ is straight or branched alkyl of 1 to 5 carbon atoms or cycloalkyl of 3 to 5 carbon atoms,
      (f) a group of the formula —$NR^9R^{10}$, wherein $R^9$ and $R^{10}$ are each independently a hydrogen atom, alkyl of 1 to 6 carbon atoms, cycloalkyl of 3 to 6 carbon atoms or acyl of 1 to 7 carbon atoms, or wherein $R^9$ and $R^{10}$ together form a saturated hydrocarbon bridge of 3 to 5 carbon atoms which together with the nitrogen atom between them form a heterocyclic ring, (g) a group of the formula —$CONR^{11}R^{12}$, wherein $R^{11}$ and $R^{12}$ are each independently a hydrogen atom, alkyl of 1 to 6 carbon atoms or cycloalkyl of 3 to 6 carbon atoms, or wherein $R^{11}$ and $R^{12}$ together form a saturated hydrocarbon bridge of 3 to 5 carbon atoms which together with the nitrogen atom between them form a heterocyclic ring,
      (h) a group of the formula —$OR^{13}$, wherein $R^{13}$ is a hydrogen atom, or an alkyl or acyl group of 1 to 7 carbon atoms,
      (i) a group of the formula —$SR^{14}$, wherein $R^{14}$ is a hydrogen atom, or an alkyl or acyl group of 1 to 7 carbon atoms,
      (j) cyano, or
      (k) an amidino group of the formula:

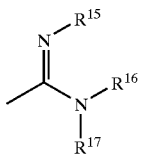

wherein $R^{15}$, $R^{16}$ and $R^{17}$ are each, independently, a hydrogen atom or alkyl of 1 to 3 carbon atoms or wherein one of $R^{15}$, $R^{16}$ and $R^{17}$ is a hydrogen atom or alkyl of 1 to 3 carbon atoms and wherein the remaining two of $R^{15}$, $R^{16}$ and $R^{17}$ together form a saturated hydrocarbon bridge of 3 to 5 carbon atoms which together with the nitrogen atom(s) between them form a heterocyclic ring,
    (iii) a group of the formula —$COOR^{18}$, wherein $R^{18}$ is straight or branched alkyl of 1 to 7 carbon atoms or cycloalkyl of 3 to 6 carbon atoms,
    (iv) a group of the formula —$CONR^{19}R^{20}$, wherein $R^{19}$ and $R^{20}$ are each, independently, a hydrogen atom, alkyl of 1 to 6 carbon atoms or cycloalkyl of 3 to 6 carbon atoms, or wherein $R^{19}$ and $R^{20}$ together form a saturated hydrocarbon bridge of 3 to 5 carbon atoms which together with the nitrogen atom between them form a heterocyclic ring,
    (v) a group of the formula —$OR^{21}$, wherein $R^{21}$ is a hydrogen atom, or an alkyl or acyl group of 1 to 7 carbon atoms,
    (vi) a group of the formula —$NR^{23}R^{24}$, wherein $R^{23}$ and $R^{24}$ are each, independently,
      (a) a hydrogen atom,
      (b) alkyl or acyl of 1 to 7 carbon atoms or cycloalkyl of 3 to 7 carbon atoms,
      (c) a group of the formula —$(CH_2)_mCOOH$, wherein m is 0, 1 or 2, or
      (d) a group of the formula —$(CH_2)_nCOOR^{25}$, wherein n is 0, 1 or 2, wherein $R^{25}$ is straight or branched alkyl of 1 to 6 carbon atoms,
    or wherein $R^{23}$ and $R^{24}$ together form a saturated hydrocarbon bridge of 3 to 5 carbon atoms which together with the nitrogen atom between them form a heterocyclic ring, or

49

(vii) a quaternary group of the formula:

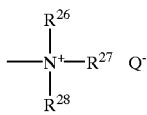

wherein $R^{26}$, $R^{27}$ and $R^{28}$ are each, independently, a branched or unbranched alkyl group of 1 to 7 carbon atoms and $Q^-$ is a chlorine, bromine or iodine counterion,
(C) a branched or unbranched carboxylic acid group of 3 to 6 carbon atoms,
(D) a branched or unbranched phosphonic acid group of 2 to 6 carbon atoms,
(E) a branched or unbranched sulfonic acid group of 2 to 6 carbon atoms,
(F) an amidino group of the formula:

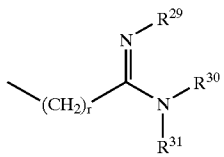

wherein r is 2, 3, 4, 5 or 6, and
$R^{29}$, $R^{30}$ and $R^{31}$ are each, independently, a hydrogen atom or alkyl of 1 to 3 carbon atoms, or wherein one of $R^{29}$, $R^{30}$ and $R^{31}$ is a hydrogen atom or alkyl of 1 to 3 carbon atoms and wherein the remaining two of $R^{29}$, $R^{30}$ and $R^{31}$ together form a saturated hydrocarbon bridge of 3 to 5 carbon atoms which together with the nitrogen atom(s) between them form a heterocyclic ring,
(G) an guanidino group of the formula:

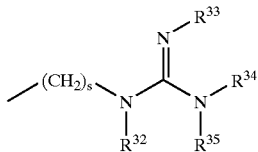

wherein s is 2, 3, 4, 5 or 6, and
$R^{32}$, $R^{33}$, $R^{34}$ and $R^{35}$ are each, independently, a hydrogen atom or alkyl of 1 to 3 carbon atoms, or wherein two of $R^{32}$, $R^{33}$, $R^{34}$ and $R^{35}$ are each, independently, a hydrogen atom or alkyl of 1 to 3 carbon atoms and wherein the remaining two of $R^{32}$, $R^{33}$, $R^{34}$ and $R^{35}$ together form a saturated hydrocarbon bridge of 3 to 5 carbon atoms which together with the nitrogen atom(s) between them form a heterocyclic ring,
(H) phenyl,
wherein one or more hydrogen atoms of said phenyl group is optionally and independently replaced with:
(i) alkyl of 1 to 3 carbon atoms,
(ii) —COOH,
(iii) —SO$_2$OH,
(iv) —PO(OH)$_2$,
(v) a group of the formula —COOR$^{36}$, wherein $R^{36}$ is straight or branched alkyl of 1 to 5 carbon atoms or cycloalkyl of 3 to 5 carbon atoms,

50

(vi) a group of the formula —NR$^{37}$R$^{38}$, wherein $R^{37}$ and $R^{38}$ are each, independently, a hydrogen atom, alkyl of 1 to 6 carbon atoms, cycloalkyl of 3 to 6 carbon atoms or acyl of 1 to 7 carbon atoms, or wherein $R^{37}$ and $R^{38}$ together form a saturated hydrocarbon bridge of 3 to 5 carbon atoms which together with the nitrogen atom between them form a heterocyclic ring,
(vii) a group of the formula —CONR$^{39}$R$^{40}$, wherein $R^{39}$ and $R^{40}$ are each, independently, a hydrogen atom, alkyl of 1 to 6 carbon atoms or cycloalkyl of 3 to 6 carbon atoms, or wherein $R^{39}$ and $R^{40}$ together form a saturated hydrocarbon bridge of 3 to 5 carbon atoms which together with the nitrogen atom between them form a heterocyclic ring,
(viii) a group of the formula —OR$^{41}$, wherein $R^{41}$ is a hydrogen atom, or an alkyl or acyl group of 1 to 7 carbon atoms,
(ix) a group of the formula —SR$^{42}$, wherein $R^{42}$ is a hydrogen atom, or an alkyl or acyl group of 1 to 7 carbon atoms,
(x) cyano, or
(xi) an amidino group of the formula:

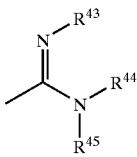

wherein $R^{43}$, $R^{44}$ and $R^{45}$ are each, independently, a hydrogen atom or alkyl of 1 to 3 carbon atoms, or wherein one of $R^{43}$, $R^{44}$ and $R^{45}$ is a hydrogen atom or alkyl of 1 to 3 carbon atoms and wherein the remaining two of $R^{43}$, $R^{44}$ and $R^{45}$ together form a saturated hydrocarbon bridge of 3 to 5 carbon atoms which together with the nitrogen atom(s) between them form a heterocyclic ring,
(I) a group of the formula —NR$^{46}$R$^{47}$, wherein $R^{46}$ and $R^{47}$ are each independently a hydrogen atom, alkyl of 1 to 6 carbon atoms, cycloalkyl of 3 to 6 carbon atoms or acyl of 1 to 7 carbon atoms, or wherein $R^{46}$ and $R^{47}$ together form a saturated hydrocarbon bridge of 3 to 5 carbon atoms which together with the nitrogen atom between them form a heterocyclic ring,
(J) a morpholinyl moiety, or,
(K) halogen;
X is an oxygen atom;
$R^3$ is:
(A) branched or unbranched alkyl of 1 to 3 carbon atoms or cycloalkyl of 3 to 5 carbon atoms;
$R^4$ is a group of the formula —CH$_2$R$^{55}$, wherein;
$R^{55}$ is:
phenyl,
wherein one or more of the hydrogen atoms at the 3 and 4 positions of said phenyl group is optionally and independently replaced with:
(A) $R^{59}$, which is aryl selected from the class consisting of phenyl, 2-, 3- or 4-pyridyl, or 2-, 4- or 5-pyrimidinyl,
wherein one or more of the hydrogen atoms of said aryl group is optionally and independently replaced with:

(i) branched or unbranched alkyl of 1 to 6 carbon atoms or cycloalkyl of 3 to 6 carbon atoms, which alkyl or cycloakyl group is optionally mono- or polysubstituted with halogen or oxo,
(ii) cyano,
(iii) nitro, or
(iv) halogen,
(B) methyl,
(C) branched or unbranched alkyl of 2 to 6 carbon atoms or cycloalkyl of 3 to 6 carbon atoms, which alkyl or cycloakyl group is optionally mono- or polysubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$,
(F) a group of the formula —OR$^{73}$, wherein R$^{73}$ is a hydrogen atom, an alkyl, fluoroalkyl or acyl group of 1 to 7 carbon atoms, or R$^{59}$,
(G) a group of the formula —SR$^{74}$, wherein R$^{74}$ is a hydrogen atom, an alkyl, fluoroalkyl or acyl group of 1 to 7 carbon atoms, or R$^{59}$,
(H) cyano,
(I) nitro, or
(J) halogen;
R$^5$ is Cl;
Z is =CH—; and,
R$^7$ is Cl;
or a pharmaceutically acceptable salt thereof.

4. A compound of the formula I, in accordance with claim 1, wherein:
A$^1$, A$^2$ and A$^3$ are each =CH—;
D is =CR—, =COR$^1$—, =CCOR$^1$—, or =CSO$_2$R$^1$—, wherein R$^1$ is:
(A) a hydrogen atom,
(B) branched or unbranched alkyl of 1 to 6 carbon atoms or cycloalkyl of 3 to 6 carbon atoms, which alkyl or cycloakyl group is optionally mono- or polysubstituted with:
(i) oxo,
(ii) phenyl,
wherein one or more hydrogen atoms of said phenyl group is optionally and independently replaced with:
(a) alkyl of 1 to 3 carbon atoms,
(b) —COOH,
(c) —SO$_2$OH,
(d) —PO(OH)$_2$,
(e) a group of the formula —COOR$^8$, wherein R$^8$ is straight or branched alkyl of 1 to 5 carbon atoms or cycloalkyl of 3 to 5 carbon atoms,
(f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ together form a saturated hydrocarbon bridge of 3 to 5 carbon atoms which together with the nitrogen atom between them form a heterocyclic ring,
(g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ together form a saturated hydro- carbon bridge of 3 to 5 carbon atoms which together with the nitrogen atom between them form a heterocyclic ring,
(h) a group of the formula —OR$^{13}$, wherein R$^{13}$ is a hydrogen atom, or an alkyl or acyl group of 1 to 7 carbon atoms,
(i) a group of the formula —SR$^{14}$, wherein R$^{14}$ is a hydrogen atom, or an alkyl or acyl group of 1 to 7 carbon atoms,
(j) cyano, or
(k) an amidino group of the formula:

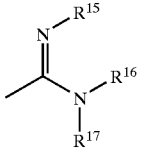

wherein R$^{15}$, R$^{16}$ and R$^{17}$ are each, independently, a hydrogen atom or alkyl of 1 to 3 carbon atoms, or wherein one of R$^{15}$, R$^{16}$ and R$^{17}$ is a hydrogen atom or alkyl of 1 to 3 carbon atoms and wherein the remaining two of R$^{15}$, R$^{16}$ and R$^{17}$ together form a saturated hydrocarbon bridge of 3 to 5 carbon atoms which together with the nitrogen atom(s) between them form a heterocyclic ring,
(iii) a group of the formula —COOR$^{18}$, wherein R$^{18}$ is straight or branched alkyl of 1 to 7 carbon atoms or cycloalkyl of 3 to 6 carbon atoms,
(iv) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ together form a saturated hydrocarbon bridge of 3 to 5 carbon atoms which together with the nitrogen atom between them form a heterocyclic ring,
(v) a group of the formula —OR$^{21}$, wherein R$^{21}$ is a hydrogen atom, or an alkyl or acyl group of 1 to 7 carbon atoms,
(vi) a group of the formula —NR$^{23}$R$^{24}$, wherein R$^{23}$ and R$^{24}$ are each, independently,
(a) a hydrogen atom,
(b) alkyl or acyl of 1 to 7 carbon atoms or cycloalkyl of 3 to 7 carbon atoms,
(c) a group of the formula —(CH$_2$)$_m$COOH, wherein m is 0, 1 or 2, or
(d) a group of the formula —(CH$_2$)$_n$COOR$^{25}$, wherein n is 0, 1 or 2, wherein R$^{25}$ is straight or branched alkyl of 1 to 6 carbon atoms,
or wherein R$^{23}$ and R$^{24}$ together form a saturated hydrocarbon bridge of 3 to 5 carbon atoms which together with the nitrogen atom between them form a heterocyclic ring, or
(vii) a quaternary group of the formula:

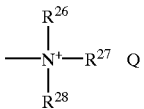

wherein R$^{26}$, R$^{27}$ and R$^{28}$ are each, independently, a branched or unbranched alkyl group of 1 to 7 carbon atoms and Q$^-$ is a chlorine, bromine or iodine counterion,
(C) a branched or unbranched carboxylic acid group of 3 to 6 carbon atoms, (D) a branched or unbranched phosphonic acid group of 2 to 6 carbon atoms,
(E) a branched or unbranched sulfonic acid group of 2 to 6 carbon atoms,
(F) an amidino group of the formula:

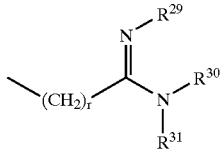

wherein r is 2, 3, 4, 5 or 6, and
$R^{29}$, $R^{30}$ and $R^{31}$ are each, independently, a hydrogen atom or alkyl of 1 to 3 carbon atoms, or wherein one of $R^{29}$, $R^{30}$ and $R^{31}$ is a hydrogen atom or alkyl of 1 to 3 carbon atoms and wherein the remaining two of $R^{29}$, $R^{30}$ and $R^{31}$ together form a saturated hydrocarbon bridge of 3 to 5 carbon atoms which together with the nitrogen atom(s) between them form a heterocyclic ring,
(G) an guanidino group of the formula:

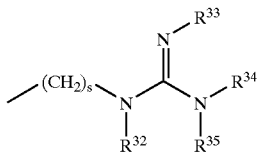

wherein s is 2, 3, 4, 5 or 6, and
$R^{32}$, $R^{33}$, $R^{34}$ and $R^{35}$ are each, independently, a hydrogen atom or alkyl of 1 to 3 carbon atoms, or wherein two of $R^{32}$, $R^{33}$, $R^{34}$ and $R^{35}$ are each, independently, a hydrogen atom or alkyl of 1 to 3 carbon atoms and wherein the remaining two of $R^{32}$, $R^{33}$, $R^{34}$ and $R^{35}$ together form a saturated hydrocarbon bridge of 3 to 5 carbon atoms which together with the nitrogen atom(s) between them form a heterocyclic ring,
(H) phenyl,
 wherein one or more hydrogen atoms of said phenyl group is optionally and independently replaced with:
  (i) alkyl of 1 to 3 carbon atoms,
  (ii) —COOH,
  (iii) —SO$_2$OH,
  (iv) —PO(OH)$_2$,
  (v) a group of the formula —COOR$^{36}$, wherein R$^{36}$ is straight or branched alkyl of 1 to 5 carbon atoms or cycloalkyl of 3 to 5 carbon atoms,
  (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ together form a saturated hydrocarbon bridge of 3 to 5 carbon atoms which together with the nitrogen atom between them form a heterocyclic ring,
  (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ together form a saturated hydrocarbon bridge of 3 to 5 carbon atoms which together with the nitrogen atom between them form a heterocyclic ring,
  (viii) a group of the formula —OR$^{41}$, wherein R$^{41}$ is a hydrogen atom, or an alkyl or acyl group of 1 to 7 carbon atoms,
  (ix) a group of the formula —SR$^{42}$, wherein R$^{42}$ is a hydrogen atom, or an alkyl or acyl group of 1 to 7 carbon atoms,
  (x) cyano, or
  (xi) an amidino group of the formula:

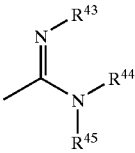

wherein $R^{43}$, $R^{44}$ and $R^{45}$ are each, independently, a hydrogen atom or alkyl of 1 to 3 carbon atoms, or wherein one of $R^{43}$, $R^{44}$ and $R^{45}$ is a hydrogen atom or alkyl of 1 to 3 carbon atoms and wherein the remaining two of $R^{43}$, $R^{44}$ and $R^{45}$ together form a saturated hydrocarbon bridge of 3 to 5 carbon atoms which together with the nitrogen atom(s) between them form a heterocyclic ring,
(I) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ together form a saturated hydrocarbon bridge of 3 to 5 carbon atoms which together with the nitrogen atom between them form a heterocyclic ring,
(J) a morpholinyl moiety, or,
(K) halogen;
X is an oxygen atom;
R$^3$ is:
 (A) branched or unbranched alkyl of 1 to 3 carbon atoms or cycloalkyl of 3 to 5 carbon atoms;
R$^4$ is a group of the formula —CH$_2$R$^{55}$, wherein;
 R$^{55}$ is:
  phenyl,
  wherein one or more of the hydrogen atoms at the 3 and 4 positions of said phenyl group is optionally and independently replaced with:
   (A) R$^{59}$, which is aryl selected from the class consisting of phenyl,
   2-, 3- or 4-pyridyl, or 2-, 4- or 5-pyrimidinyl, wherein one or more of the hydrogen atoms of said aryl group is optionally and independently replaced with:
    (i) branched or unbranched alkyl of 1 to 6 carbon atoms or cycloalkyl of 3 to 6 carbon atoms, which alkyl or cycloakyl group is optionally mono- or polysubstituted with halogen or oxo,
    (ii) cyano,
    (iii) nitro, or
    (iv) halogen,
   (B) methyl,
   (C) branched or unbranched alkyl of 2 to 6 carbon atoms or cycloalkyl of 3 to 6 carbon atoms, which alkyl or cycloakyl group is optionally mono- or polysubstituted with halogen or oxo,
   (D) a group of the formula —COOR$^{67}$, wherein R$^{67}$ is straight or branched alkyl of 1 to 5 carbon atoms or cycloalkyl of 3 to 5 carbon atoms, (E) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$,
(F) a group of the formula —OR$^{73}$, wherein R$^{73}$ is a hydrogen atom, an alkyl, fluoroalkyl or acyl group of 1 to 7 carbon atoms, or R$^{59}$,
(G) a group of the formula —SR$^{74}$, wherein R$^{74}$ is a hydrogen atom, an alkyl, fluoroalkyl or acyl group of 1 to 7 carbon atoms, or R$^{59}$,
(H) cyano,
(I) nitro, or
(J) halogen;

R$^5$ is Cl;
Z is =CH—; and,
R$^7$ is Cl;
or a pharmaceutically acceptable salt thereof.

5. A compound of the formula I, in accordance with claim 1, wherein:
A$^1$, A$^2$ and A$^3$ are each =CH—;
D is =CCOR$^1$— or =CSO$_2$R$^1$—,
  R$^1$ is:
  (A) a hydrogen atom,
  (B) branched or unbranched alkyl of 1 to 6 carbon atoms or cycloalkyl of 3 to 6 carbon atoms, which alkyl or cycloakyl group is optionally mono- or polysubstituted with:
    (i) oxo,
    (ii) a group of the formula —COOR$^{18}$, wherein R$^{18}$ is straight or branched alkyl of 1 to 7 carbon atoms or cycloalkyl of 3 to 6 carbon atoms,
    (iii) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ together form a saturated hydrocarbon bridge of 3 to 5 carbon atoms which together with the nitrogen atom between them form a heterocyclic ring,
    (iv) a group of the formula —OR$^{21}$, wherein R$^{21}$ is a hydrogen atom, or an alkyl or acyl group of 1 to 7 carbon atoms,
    (v) a group of the formula —NR$^{23}$R$^{24}$, wherein R$^{23}$ and R$^{24}$ are each, independently,
      (a) a hydrogen atom,
      (b) alkyl or acyl of 1 to 7 carbon atoms or cycloalkyl of 3 to 7 carbon atoms,
      (c) a group of the formula —(CH$_2$)$_m$COOH, wherein m is 0, 1 or 2, or
      (d) a group of the formula —(CH$_2$)$_n$COOR$^{25}$, wherein n is 0, 1 or 2, wherein R$^{25}$ is straight or branched alkyl of 1 to 6 carbon atoms,
    or wherein R$^{23}$ and R$^{24}$ together form a saturated hydrocarbon bridge of 3 to 5 carbon atoms which together with the nitrogen atom between them form a heterocyclic ring, or
    (vi) a quaternary group of the formula:

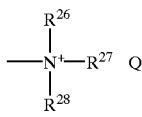

wherein R$^{26}$, R$^{27}$ and R$^{28}$ are each, independently, a branched or unbranched alkyl group of 1 to 7 carbon atoms and Q$^-$ is a chlorine, bromine or iodine counterion,
  (C) a branched or unbranched carboxylic acid group of 3 to 6 carbon atoms,
  (D) a branched or unbranched phosphonic acid group of 2 to 6 carbon atoms,
  (E) a branched or unbranched sulfonic acid group of 2 to 6 carbon atoms,
  (F) an amidino group of the formula:

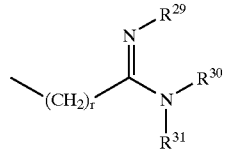

wherein r is 2, 3, 4, 5 or 6, and
    R$^{29}$, R$^{30}$ and R$^{31}$ are each, independently, a hydrogen atom or alkyl of 1 to 3 carbon atoms, or wherein one of R$^{29}$, R$^{30}$ and R$^{31}$ is a hydrogen atom or alkyl of 1 to 3 carbon atoms and wherein the remaining two of R$^{29}$, R$^{30}$ and R$^{31}$ together form a saturated hydrocarbon bridge of 3 to 5 carbon atoms which together with the nitrogen atom(s) between them form a heterocyclic ring,
  (G) an guanidino group of the formula:

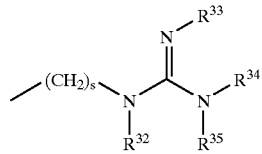

wherein s is 2, 3, 4, 5 or 6, and
    R$^{32}$, R$^{33}$, R$^{34}$ and R$^{35}$ are each, independently, a hydrogen atom or alkyl of 1 to 3 carbon atoms, or wherein two of R$^{32}$, R$^{33}$, R$^{34}$ and R$^{35}$ are each, independently, a hydrogen atom or alkyl of 1 to 3 carbon atoms and wherein the remaining two of R$^{32}$, R$^{33}$, R$^{34}$ and R$^{35}$ together form a saturated hydrocarbon bridge of 3 to 5 carbon atoms which together with the nitrogen atom(s) between them form a heterocyclic ring,
  (H) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ together form a saturated hydrocarbon bridge of 3 to 5 carbon atoms which together with the nitrogen atom between them form a heterocyclic ring,
  (I) a morpholinyl moiety, or,
  (J) halogen;
X is an oxygen atom;
R$^3$ is:
  (A) branched or unbranched alkyl of 1 to 3 carbon atoms or cycloalkyl of 3 to 5 carbon atoms;
R$^4$ is a group of the formula —CH$_2$R$^{55}$, wherein;
R$^{55}$ is:
  phenyl, wherein one or more of the hydrogen atoms at the 3 and 4 positions of said phenyl group is optionally and independently replaced with:
    (A) R$^{59}$, which is aryl selected from the class consisting of phenyl, 2-, 3- or 4-pyridyl, or 2-, 4- or 5-pyrimidinyl, wherein one or more of the hydrogen atoms of said aryl group is optionally and independently replaced with:
      (i) branched or unbranched alkyl of 1 to 6 carbon atoms or cycloalkyl of 3 to 6 carbon atoms, which alkyl or cycloakyl group is optionally mono- or polysubstituted with halogen or oxo,
(ii) cyano,
(iii) nitro, or
(iv) halogen,
(B) methyl,
(C) branched or unbranched alkyl of 2 to 6 carbon atoms or cycloalkyl of 3 to 6 carbon atoms, which alkyl or cycloakyl group is optionally mono- or polysubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —COR$^{72}$, wherein R$^{72}$ is a hydrogen atom, straight or branched alkyl of 1 to 5 carbon atoms, cycloalkyl of 3 to 5 carbon atoms or R$^{59}$,
(F) a group of the formula —OR$^{73}$, wherein R$^{73}$ is a hydrogen atom, an alkyl, fluoroalkyl or acyl group of 1 to 7 carbon atoms, or R$^{59}$,
(G) a group of the formula —SR$^{74}$, wherein R$^{74}$ is a hydrogen atom, an alkyl, fluoroalkyl or acyl group of 1 to 7 carbon atoms, or R$^{59}$,
(H) cyano,
(I) nitro, or
(J) halogen;
R$^5$ is Cl;
Z is =CH—; and,
R$^7$ is Cl;
or a pharmaceutically acceptable salt thereof.

6. A compound of the formula I, in accordance with claim 1, wherein:
A$^1$, A$^2$ and A$^3$ are each =CH—;
D is =CCOR$^1$— or =CSO$_2$R$^1$—,
R$^1$ is
(A) a hydrogen atom,
(B) branched or unbranched alkyl of 1 to 6 carbon atoms or cycloalkyl of 3 to 6 carbon atoms, which alkyl or cycloakyl group is optionally mono- or polysubstituted with a group of the formula —OR$^{21}$, wherein R$^{21}$ is a hydrogen atom, or an alkyl or acyl group of 1 to 7 carbon atoms,
(C) a group of the formula —NR$^{46}$R$^{47}$, wherein R$^{46}$ and R$^{47}$ are each independently a hydrogen atom, alkyl of 1 to 6 carbon atoms, cycloalkyl of 3 to 6 carbon atoms or acyl of 1 to 7 carbon atoms, or wherein R$^{46}$ and R$^{47}$ together form a saturated hydrocarbon bridge of 3 to 5 carbon atoms which together with the nitrogen atom between them form a heterocyclic ring, or
(D) a morpholinyl moiety;
X is an oxygen atom;
R$^3$ is methyl;
R$^4$ is a group of the formula —CH$_2$R$^{55}$, wherein;
R$^{55}$ is:
phenyl, wherein one or more of the hydrogen atoms at the 4 position of said phenyl group is optionally and independently replaced with:
(A) R$^{59}$, which is aryl selected from the class consisting of phenyl, 3-pyridyl, or 5-pyrimidinyl, wherein one or more of the hydrogen atoms of said aryl group is optionally and independently replaced with:
(i) methyl,
(ii) cyano,
(iii) nitro, or
(iv) halogen,
(B) methyl,
(C) cyano,
(D) nitro, or
(E) halogen;
R$^5$ is Cl;
Z is =CH—; and,
R$^7$ is Cl;
or a pharmaceutically acceptable salt thereof.

7. A compound selected from the group consisting of:
3-(4-bromobenzyl)-1-(3,5-dichlorophenyl)-1,3-dihydroindol-1,3-2-one;
3-(4-bromobenzyl)-1-(3,5-dichlorophenyl)-3-methyl-1,3-dihydroindol-2-one;
3-benzyl-1-(3,5-dichlorophenyl)-3-methyl-1,3-dihydroindol-2-one;
3-(4-bromobenzyl)-1-(3,5-dichlorophenyl)-4-hydroxy-3-methyl-1,3-dihydroindol-2-one;
3-(4-bromobenzyl)-1-(3,5-dichlorophenyl)-5-fluoro-1,3-dihydroindol-2-one;
3-(4-bromobenzyl)-1-(3,5-dichlorophenyl)-1,3-dihydroindol-2-one-6-carboxylic acid;
3-benzyl-1-(3,5-dichlorophenyl)-4-methoxy-1,3-dihydroindol-2-one;
3-(3-bromobenzyl)-1-(3,5-dichlorophenyl)-4-methoxy-1,3-dihydroindol-2-one;
3-(3-bromobenzyl)-1-(3,5-dichlorophenyl)-4-hydroxy-3-methyl-1,3-dihydroindol-2-one;
3-benzyl-1-(3,5-dichlorophenyl)-4-hydroxy-1,3-dihydroindol-2-one;
3-benzyl-1-(3,5-dichlorophenyl)-4-methoxy-1,3-dihydroindol-2-one;
3-benzyl-1-(3,5-dichlorophenyl)-5-hydroxy-1,3-dihydroindol-2-one;
3-benzyl-1-(3,5-dichlorophenyl)-1,3-dihydroindol-2-one;
3-benzyl-1-(3,5-dichlorophenyl)-4-hydroxy-3-methyl-1,3-dihydroindol-2-one;
3-(4-bromobenzyl)-1-(3,5-dichlorophenyl)-4-hydroxy-1,3-dihydroindol-2-one;
3-(4-bromobenzyl)-1-(3,5-dichlorophenyl)-3-methyl-1,3-dihydropyrrolo[2,3-b]pyridin-2-one; and,
3-(4-cyanobenzyl)-1-(3,5-dichlorophenyl)-3-methyl-1,3dihydropyrrolo[2,3-b]pyridin-2-one;
or a pharmaceutically acceptable salt thereof.

8. A compound in accordance with claim 1, 2, 3, 4, 5, 6 or 7, having the absolute stereochemistry depicted below in formula Ia:

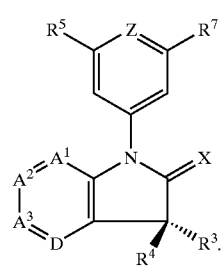

9. A method for the treatment of an inflammatory or immune cell-mediated disease or condition which comprises administering to a host in need or such treatment a therapeutic amount of a compound of the formula I in accordance with claim 1, 2, 3, 4, 5, 6 or 7.

10. The method of claim 9 wherein the disease or condition is selected from the group consisting of adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome.

11. The method of claim 9 wherein the disease or condition is selected from the group consisting of psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis; and systemic lupus erythematosus.

12. The method of claim 9 wherein the disease or condition is asthma.

13. The method of claim 9 wherein the disease or condition is psoriasis.

14. A pharmaceutical composition comprising a compound in accordance with claim 1, 2, 3, 4, 5, 6, 7 or 8 and a pharmaceutically acceptable carrier or diluent.

* * * * *